US008877732B2

(12) United States Patent
Kim et al.

(10) Patent No.: US 8,877,732 B2
(45) Date of Patent: Nov. 4, 2014

(54) COMBINATION, KIT AND METHOD OF REDUCING INTRAOCULAR PRESSURE

(75) Inventors: Norman N. Kim, Westford, MA (US); William K. McVicar, Sudbury, MA (US); Thomas G. McCauley, Cambridge, MA (US); Rudolf A. Baumgartner, Sudbury, MA (US)

(73) Assignee: Inotek Pharmaceuticals Corporation, Lexington, MA (US)

( * ) Notice: Subject to any disclaimer, the term of this patent is extended or adjusted under 35 U.S.C. 154(b) by 435 days.

(21) Appl. No.: 13/004,380

(22) Filed: Jan. 11, 2011

(65) Prior Publication Data

US 2011/0172177 A1 Jul. 14, 2011

Related U.S. Application Data

(60) Provisional application No. 61/293,806, filed on Jan. 11, 2010.

(51) Int. Cl.

| | |
|---|---|
| ***A61K 31/70*** | (2006.01) |
| ***A61K 31/24*** | (2006.01) |
| ***A61K 31/215*** | (2006.01) |
| ***A61K 31/235*** | (2006.01) |
| ***A01N 43/04*** | (2006.01) |
| ***A01N 37/08*** | (2006.01) |
| ***A01N 37/10*** | (2006.01) |
| ***A61K 9/00*** | (2006.01) |
| ***A61K 45/06*** | (2006.01) |
| ***A61K 31/7076*** | (2006.01) |
| ***A61K 31/19*** | (2006.01) |
| ***A61K 31/165*** | (2006.01) |
| ***A61K 31/216*** | (2006.01) |
| *A01N 37/12* | (2006.01) |
| *A01N 37/44* | (2006.01) |

(52) U.S. Cl.

CPC .............. *A61K 45/06* (2013.01); *A61K 9/0048* (2013.01); *A61K 31/7076* (2013.01); *A61K 31/19* (2013.01); *A61K 31/165* (2013.01); *A61K 31/216* (2013.01)

USPC .............. 514/46; 514/530; 514/532; 514/537

(58) Field of Classification Search

None

See application file for complete search history.

(56) References Cited

U.S. PATENT DOCUMENTS

| | | | | |
|---|---|---|---|---|
| 5,221,763 | A * | 6/1993 | Ueno et al. | 560/121 |
| 5,296,504 | A | 3/1994 | Stjernschantz et al. | |
| 5,422,368 | A | 6/1995 | Stjernschantz et al. | |
| 5,591,887 | A * | 1/1997 | Ueno et al. | 560/121 |
| 5,770,759 | A * | 6/1998 | Ueno et al. | 560/53 |
| 6,403,649 | B1 * | 6/2002 | Woodward et al. | 514/646 |
| 6,429,229 | B1 | 8/2002 | Bouyssou et al. | |
| 7,163,959 | B2 | 1/2007 | Stjernschantz et al. | |
| 7,732,424 | B2 * | 6/2010 | Jagtap et al. | 514/46 |

FOREIGN PATENT DOCUMENTS

| | | | |
|---|---|---|---|
| CN | 101010085 | | 8/2007 |
| EP | 0 364 417 | A1 * | 4/1990 |
| WO | WO 93/00329 | A1 * | 1/1993 |
| WO | 02/09702 | A2 | 2/2002 |
| WO | 2005/117910 | A2 | 12/2005 |
| WO | 2007/064795 | A2 | 6/2007 |
| WO | 2010/127210 | A1 | 11/2010 |

OTHER PUBLICATIONS (R) M. J. O'Neil et al. (eds.), "The Merck Index, 14th Edition," Merck & Co., Whitehouse Station, NJ, 2006, only pp. 1693 supplied (see "Unoprostone").*

Chinese Office Action for Application No. 201080018539.X, 9 pages, dated Nov. 2, 2012.

Avila, Marcel Y. et al., "A1-, A2A- and A3-subtype adenosine receptors modulate intraocular pressure in the mouse," British Journal of Pharmacology, vol. 134:241-245 (2001).

Camaioni, Emidio et al., "Adenosine Receptor Agonists: Synthesis and Biological Evaluation of the Diastereoisomers of 2-(3-Hydroxy-3-phenyl-1-propyn-1-yl)NECA," Bioorganic & Medicinal Chemistry, vol. 5(12):2267-2275 (1997).

(Continued)

*Primary Examiner* — Lawrence E Crane

(74) *Attorney, Agent, or Firm* — Nelson Mullins Riley & Scarborough LLP; Jane E. Remillard, Esq.; Cynthia L. Kanik

(57) ABSTRACT

The present invention is directed to a combination or a kit comprising a prostaglandin analog and an adenosine receptor $A_1$ agonist and to a method of reducing intraocular pressure (IOP) in a subject using such combination or kit. In one embodiment, the prostaglandin analog is latanoprost and the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, having the structure,

HN
N
N
N
N
H
O
OH
OH
$ONO_2$

14 Claims, 6 Drawing Sheets

(56) References Cited

OTHER PUBLICATIONS

Cristalli, Gloria et al., "2-Alkynyl Derivatives of Adenosine-5'-N-ethyluronamide: Selective A2 Adenosine Receptor Agonists with Potent Inhibitory Activity on Platelet Aggregation," J. Med. Chem., vol. 37:1720-1726 (1994).
Cristalli, Gloria et al., "2-Alkynyl Derivatives of Adenosine and Adenosine-5'N-ethyluronamide as Selective Agonists at A2 Adenosine Receptors," J. Med. Chem., vol. 35:2363-2368 (1992).
Cristalli, Gloria et al., "2-Aralkynyl and 2-Heteroalkynyl Derivatives of Adenosine-5'-N-ethyluronamide as Selective A2a Adenosine Receptor Agonists," J. Med. Chem., vol. 38:1462-1472 (1995).
Crosson, Craig E., "Adenosine Receptor Activation Modulates Intraocular Pressure in Rabbits," The Journal of Pharmacology and Experimental Therapeutics, vol. 273(1):320-326 (1995).
Crosson, Craig E., "Ocular hypotensive activity of the adenosine agonist (R)-phenylisopropyladenosine in rabbits," Current Eye Research, vol. 11(5):453-458 (1992).
Fredholm, Berth B. et al., "International Union of Pharmacology. XXV. Nomenclature and Classification of Adenosine Receptors," Pharmacological Reviews, vol. 53(4):527-552 (2001).
Husain, S. et al., "Mechanisms Linking Adenosine A1 Receptors and Extracellular Signal-Regulated Kinase 1/2 Activation in Human Trabecular Meshwork Cells," The Journal of Pharmacology and Experimental Therapeutics, vol. 320(1):258-265 (2007).
Ralevic, Vera et al., "Receptors for Purines and Pyrimidines," Pharmacological Reviews, vol. 50(3):413-492 (1998).
Stewart, William C. et al., "Beta-Blocker-Induced Complications and the Patient With Glaucoma," Archives of Internal Medicine, vol. 158(3):221-226 (1998).
Tian, Baohe et al., "Effects of Adenosine Agonists on Intraocular Pressure and Aqueous Humor Dynamics in Cynomolgus Monkeys," Exp. Eye Res., vol. 64:979-989 (1997).
International Search Report and Written Opinion for Application No. PCT/US2011/020808, dated Mar. 30, 2011.
Gandolfi, Stefano et al., "Three-Month Comparison of Bimatoprost and Latanoprost in Patients With Glaucoma and Ocular Hypertension," Advances in Therapy, vol. 18(3):110-121 (2001).
Gurwood, Andrew S., "Comparing selective laser trabeculoplasty witih Latanoprost for the control of intraocular pressure," Br. J. Ophthalmol. vol. 89(11):1413-1417 (2005).
Orzalesi, Nicola et al., "Comparison of the Effects of Latanoprost, Travoprost, and Bimatoprost on Circadian Intraocular Pressure in Patients with Glaucoma or Ocular Hypertension," Ophthalmology, vol. 113:239-246 (2006).
Supplementary European Search Report for Application No. 11732309.7, 10 pages, dated Jul. 31, 2013.

* cited by examiner

IOP (mmHg) Following Ocular Dosing of
Compound A and Prostaglandin in Normotensive Monkeys
Prostaglandin
Compound A
IOP (mmHg)
26
23
20
17
14
0
2
4
6
8
Time (hours)
IOP (% change from baseline) Following Ocular Dosing of
Compound A and Prostaglandin in Normotensive Monkeys
IOP (% change)
15
10
5
0
-5
-10
-15
-20
-25
-30
-35
Time (hours)
Vehicle
Prostaglandin, 1.5 mcg (n=20)
Prostaglandin, 1.5 mcg + Compound A, 500mcg, 0hr (n=10)

IOP (mmHg) Following Ocular Dosing of Compound A and Prostaglandin in Normotensive Monkeys
Prostaglandin
Compound A
IOP (mm Hg)
26
23
20
17
14
0
2
4
6
8
Time (hours)
IOP (% change from baseline) Following Ocular Dosing of Compound A and Prostaglandin in Normotensive Monkeys
Time (hours)
IOP (% change)
15
10
5
0
-5
-10
-15
-20
-25
-30
-35
Vehicle
Prostaglandin, 1.5 mcg (n=20)
Prostaglandin, 1.5 mcg + Compound A, 100mcg, 5hr (n=10)

Mean IOP Measured Over Several Days Following Repeated Ocular Administration
of Latanoprost Alone or in Combination with Compound A in Normotensive Monkeys
Mean IOP (mmHg)
24
22
20
18
16
0
1
2
3
4
5
6
7
8
Time (hours)
Control
Latanoprost (1.5 mcg)
Latanoprost (1.5 mcg) + Compound A (65 mcg)

Mean Percent Change from Baseline in IOP Measured Over Several Days Following Repeated Ocular Administration of Latanoprost Alone or in Combination with Compound A in Normotensive Monkeys

COMBINATION, KIT AND METHOD OF REDUCING INTRAOCULAR PRESSURE

RELATED APPLICATIONS

This application claims priority to U.S. Provisional Application No. 61/293,806, filed Jan. 11, 2010. The contents of any patents, patent applications, and references cited throughout this specification are hereby incorporated by reference in their entireties.

TECHNICAL FIELD OF THE INVENTION

The present invention is directed to a combination or a kit comprising a prostaglandin analog and an adenosine receptor $A_1$ agonist, and to a method of reducing intraocular pressure (IOP) in a subject using such combination or kit. In one embodiment, the invention is directed to a combination of latanoprost marketed under the brand Xalatan™ and Compound A.

Latanoprost is a prostaglandin $F_{2\alpha}$ analogue. Its chemical name is isopropyl-(Z)-7[(1R,2R,3R,5S)3,5-dihydroxy-2-[(3R)-3-hydroxy-5-phenylpentyl]cyclopentyl]-5-heptenoate and has the following chemical structure:

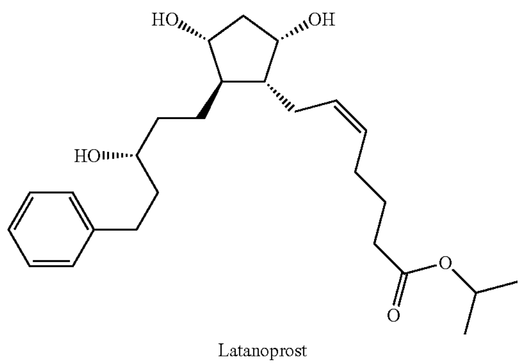 [SMILES: CC(C)OC(=O)CCC/C=C\C[C@@H]1[C@@H](CC[C@@H](O)CCc2ccccc2)[C@H](O)C[C@@H]1O]

Latanoprost

Compound A is an adenosine receptor $A_1$ agonist and has the following structure:

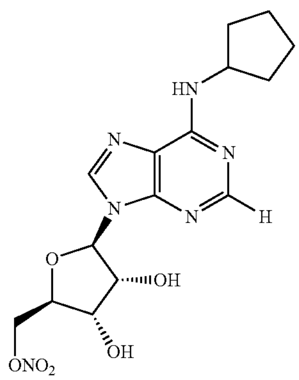

((2R,3S,4R,5R)-5-(6-(cyclopentylamino)-9H-purin-9-yl)-3,4-dihydroxytetrahydrofuran-2-yl)methyl nitrate.

BACKGROUND OF THE INVENTION

Glaucoma refers to a group of optic neuropathies that are characterized by loss of retinal ganglion cells and atrophy of the optic nerve with resultant visual field loss. The disease is the leading cause of irreversible blindness worldwide and the second leading cause of blindness, behind cataracts. Clinical trials have demonstrated that elevated IOP is a major risk factor for glaucoma and have validated the role of lowering IOP in the management of glaucoma.

Glaucoma is classified according to three parameters: 1) the underlying cause, i.e., primary (idiopathic) or secondary (associated with some other ocular or systemic conditions); 2) the state of the anterior chamber angle, i.e., open angle (open access of the outflowing aqueous humor to trabecular meshwork) or closed angle (narrow angle; the trabecular meshwork is blocked by apposition of the peripheral iris and the cornea); and 3) chronicity, i.e., acute or chronic. Although secondary forms of glaucoma with clear etiologies do exist (e.g., pseudoexfoliation and pigmentary dispersion), the most common form of glaucoma is primary open angle glaucoma (POAG).

Occular Hypertension (OHT) is a condition in which IOP is elevated but no glaucomatous findings have been observed (Bell and Charleton, 2011—http://emedicine.medscape.com/article/1207470-overview). The Ocular Hypertension Study demonstrated that patients with OHT have an overall risk of 10% over 5 years of developing glaucoma and that this risk can be cut in half by the institution of medical treatment that reduces IOP. Latanoprost is described in, for example, U.S. Pat. Nos. 5,296,504; 5,422,368; 6,429,229 and 7,163,959, all of which are incorporated herein by reference in their entirety.

Latanoprost has been used as a topical ophthalmic medication for controlling the progression of glaucoma or ocular hypertension by reducing intraocular pressure. It is a prostaglandin analogue that works by increasing the outflow of aqueous fluid from the eyes (through the uveoscleral tract). Latanoprost, which is marketed as Xalatan™ is indicated for the reduction of elevated intraocular pressure in patients with open-angle glaucoma or ocular hypertension.

Applicant has been conducting clinical studies with an $A_1$ agonist. These studies have been described in co-pending application WO 2010/127210. The Applicant has shown clinically significant reduction of intraocular pressure using an $A_1$ agonist in human subjects having glaucoma. The specifications of WO 2010/127210 are herein incorporated in their entirety as if individually set forth.

Applicant has recently conducted pre-clinical studies and found that the use of a combination of an $A_1$ agonist, specifically Compound A, and a prostaglandin analog, specifically latanoprost, provided significant IOP reduction in normotensive monkeys.

SUMMARY OF THE INVENTION

There remains a need for new treatments and therapies for elevated intraocular pressure (IOP), and conditions caused by elevated IOP. There is also a need for compounds useful in the treatment or prevention or amelioration of one or more symptoms of elevated IOP and conditions caused by elevated IOP.

Thus, provided herein is a combination therapy, comprising an effective amount of an adenosine receptor $A_1$ agonist (e.g. a compound of Formula I), and an effective amount of a prostaglandin analog (e.g. latanoprost). This combination can be useful for the treatment of one or more symptoms of elevated IOP and conditions caused by elevated IOP, e.g., glaucoma.

In a first aspect there is provided an ophthalmic combination comprising i) an adenosine receptor $A_1$ agonist and ii) a prostaglandin analog for use in reducing intraocular pressure in an eye of a subject.

In one embodiment the prostaglandin analog is selected from latanoprost, travoprost, unoprostone and bimatoprost.

In another embodiment the prostaglandin analog is latanoprost.

In one embodiment the adenosine receptor $A_1$ agonist is selected from a compound of Formula (I)

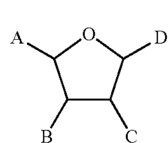

(I)

or a pharmaceutically acceptable salt thereof, wherein

A is —$CH_2OH$, —$CH_2ONO_2$ or —$CH_2OSO_3H$;

B and C are —OH;

D is

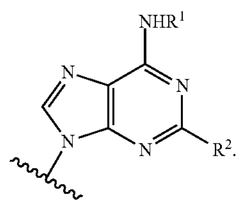

In a further embodiment the compound of Formula I is selected from:

Compound A [((2R,3S,4R,5R)-5-(6-(cyclopentylamino)-9H-purin-9-yl)-3,4-dihydroxytetrahydrofuran-2-yl)methyl nitrate];

Compound B [((2R,3S,4R,5R)-5-(2-chloro-6-(cyclopentylamino)-9H-purin-9-yl)-3,4-dihydroxytetrahydrofuran-2-yl) methyl nitrate];

Compound C [sodium ((2R,3S,4R,5R)-5-(6-(cyclopentylamino)-9H-purin-9-yl)-3,4-dihydroxytetrahydrofuran-2-yl) methyl sulfate];

Compound D [((2R,3S,4R,5R)-3,4-dihydroxy-5-(6-(tetrahydrofuran-3-ylamino)-9H-purin-9-yl)tetrahydrofuran-2-yl) methyl nitrate];

Compound E [((2R,3S,4R,5R)-5-(6-(cyclohexylamino)-9H-purin-9-yl)-3,4-dihydroxytetrahydrofuran-2-yl)methyl nitrate];

Compound F [((2R,3S,4R,5R)-5-(6-(bicycle-[2.2.1]-heptan-2-ylamino)-9H-purin-9-yl)-3,4-dihydroxytetrahydrofuran-2-yl)methyl nitrate];

Compound G [sodium ((2R,3S,4R,5R)-5-(2-chloro-6-(cyclohexylamino)-9H-purin-9-yl)-3,4-dihydroxytetrahydrofuran-2-yl)methyl sulfate];

Compound H [((2R,3S,4R,5R)-5-(2-chloro-6-(cyclohexylamino)-9H-purin-9-yl)-3,4-dihydroxytetrahydrofuran-2-yl) methyl nitrate];

Compound I [(2R,3R,4S,5R)-2-(6-(cyclopentylamino)-9H-purin-9-yl)-5-(hydroxymethyl)tetrahydrofuran-3,4-diol (N6 Cyclopentyl adenosine (CPA))]; and Compound J [(2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (CCPA))], or a pharmaceutically acceptable salt thereof.

In a further embodiment the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof.

In still another embodiment of the ophthalmic combination, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof, and the prostaglandin analog Latanoprost.

In another embodiment the $A_1$ agonist is applied to an eye of the subject simultaneously to, separately from, or sequentially with the application of the prostaglandin analog to the eye of the subject.

In a further embodiment the combination is achieved by applying one or more drops of about 0.05 mg/ml to about 7.0 mg/ml of an $A_1$ agonist with about 30 μg/ml to about 50 μg/ml of a prostaglandin analog to an eye of the subject from 1 to 4 times daily.

In a further embodiment the combination is achieved by applying about 20-700 μg of an $A_1$ agonist to an eye of the subject from 1 to 2 times daily.

In a further embodiment the combination is achieved by applying about 20-350 μg of an $A_1$ agonist to an eye of the subject from 1 to 2 times daily. In one embodiment the $A_1$ agonist and the prostaglandin analog are administered topically as one or more eye drops to the eye of the subject.

In a further aspect there is provided a method of reducing IOP and associated diseases and conditions caused by elevated IOP in a subject by administering an effective amount of a combination as defined above to an affected eye of the subject.

In one embodiment the diseases and conditions caused by elevated IOP in a human are selected from the group consisting of normal-tension glaucoma, OHT, and POAG.

In a further aspect there is provided a kit comprising i) an adenosine receptor $A_1$ agonist and ii) a prostaglandin analog for use in reducing intraocular pressure in an eye of a subject.

In one embodiment of the kit the prostaglandin analog is selected from latanoprost, travoprost, unoprostone and bimatoprost.

In another embodiment of the kit the prostaglandin analog is latanoprost.

In a further embodiment of the kit the adenosine receptor $A_1$ agonist is selected from a compound of Formula (I)

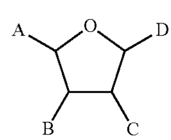

(I)

or a pharmaceutically acceptable salt thereof, wherein

A is —$CH_2OH$, —$CH_2ONO_2$ or —$CH_2OSO_3H$;

B and C are —OH;

D is

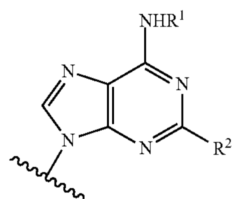

In another embodiment of the kit the compound of Formula I is selected from: Compound A, Compound B, Compound C, Compound D, Compound E, Compound F, Compound H, or Compound I.

In another embodiment of the kit, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate or a pharmaceutically acceptable salt thereof.

In still another embodiment of the kit, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost.

In one embodiment provided herein is a method of treating elevated IOP and associated diseases and conditions caused by elevated IOP in a subject by administering an effective amount of a combination comprising the adenosine receptor $A_1$ agonist Compound A, ((2R,3S,4R,5R)-5-(6-(cyclopentylamino)-9H-purin-9-yl)-3,4-dihydroxytetrahydrofuran-2-yl) methyl nitrate, and the prostaglandin analog Latanoprost.

It is to be further appreciated that the combinations or kits, as defined above, may be used in the manufacture of a medicament for reducing IOP or the treatment of conditions associated with elevated IOP, in an affected eye of a human subject. It is to be further appreciated that the combinations or kits, as defined above, may be used in the manufacture of a medicament for treating glaucoma in an affected eye of a human subject.

In one embodiment provided herein is the use of a combination of the adenosine receptor $A_1$ agonist Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost in the manufacture of a medicament for the treatment of elevated IOP and the treatment of associated diseases and conditions caused by elevated IOP.

In another aspect of the invention is provided a combination therapy, comprising an effective amount of an adenosine receptor $A_1$ agonist, and an effective amount of a prostaglandin analog.

In one embodiment, the combination therapy is for the treatment of elevated IOP. In one embodiment, the combination therapy is for the treatment of glaucoma.

The foregoing brief summary broadly describes the features and technical advantages of certain embodiments of the present invention. Further technical advantages will be described in the detailed description of the invention that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
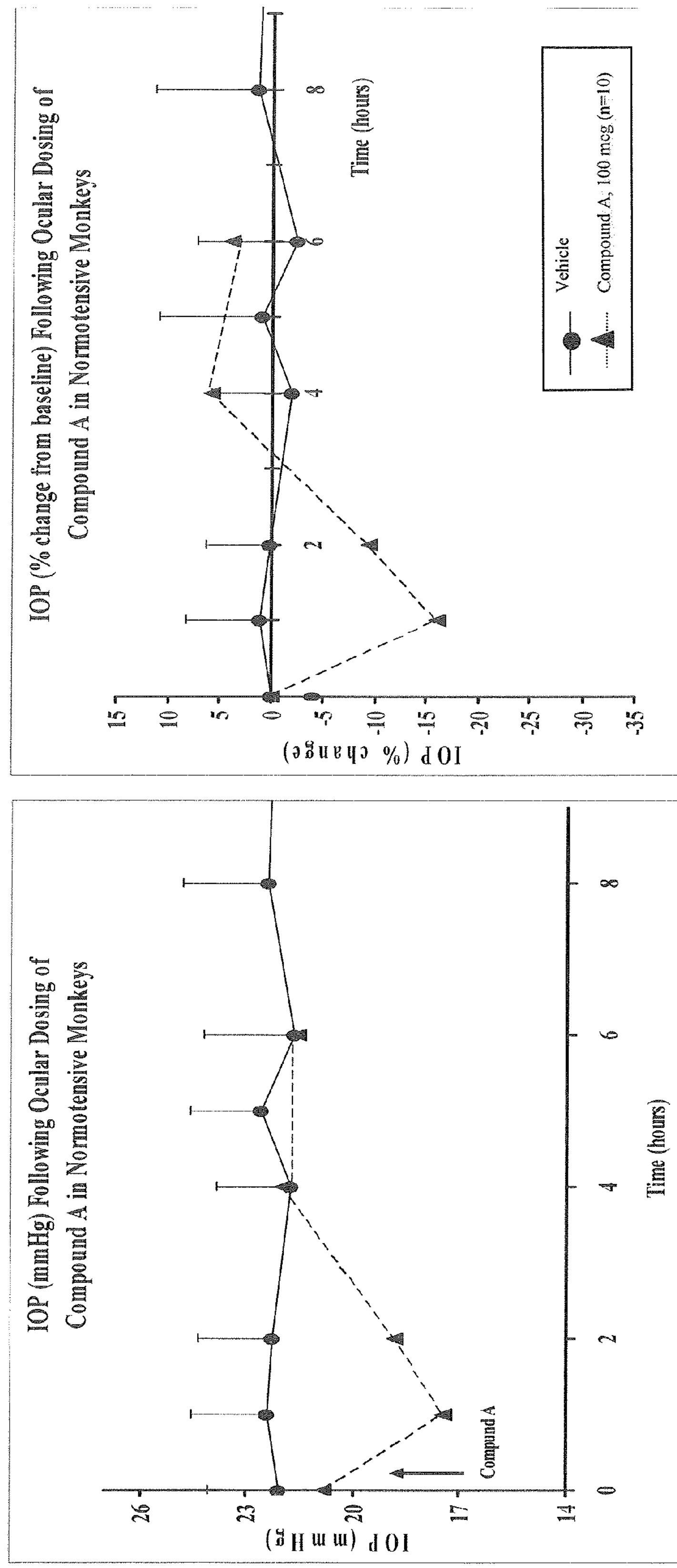
FIG. 1: shows the reduction in IOP (mmHg) in normotensive monkeys following ocular dosing of 100 mcg of Compound A at 4 hrs after ocular dosing of a prostaglandin analog compared to the reduction in IOP following dosing of a prostaglandin analog alone.

Provided herein is a combination therapy, comprising an effective amount of an adenosine receptor $A_1$ agonist (e.g., a compound of Formula I), and an effective amount of a prostaglandin analog (e.g. latanoprost, travoprost, unoprostone and bimatoprost). The combination can be used for reducing intraocular pressure in an eye of a subject in need thereof. The combination can also be useful for the treatment of diseases and conditions caused by elevated IOP in a human, such as glaucoma (e.g., normal-tension glaucoma), OHT, and POAG.

Compounds and Methods of Treatment

Compounds of Formula I have the following structure:

(I)

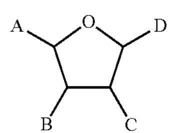

or a pharmaceutically acceptable salt thereof, wherein

A is —$CH_2OH$, —$CH_2ONO_2$ or —$CH_2OSO_3H$;

B and C are —OH;

D is

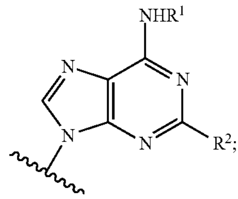

A and B are trans with respect to each other;

B and C are cis with respect to each other;

C and D are cis or trans with respect to each other;

$R^1$ is —H, —$C_1$-$C_{10}$ alkyl, -aryl, -3- to 7-membered monocyclic heterocycle, -8- to 12-membered bicyclic heterocycle, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;

$R^2$ is —H, halo, —CN, —$NHR^4$, —$NHC(O)R^4$, —$NHC(O)OR^4$, —$NHC(O)NHR^4$, —$NHNHC(O)R^4$, —$NHNHC(O)OR^4$, —$NHNHC(O)NHR^4$, or —NH—N═$C(R^6)R^7$;

$R^4$ is —$C_1$-$C_{15}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;

$R^6$ is —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)_n$COO—($C_1$-$C_{10}$ alkyl);

$R^7$ is —H, —$C_1$-$C_{10}$ alkyl, -aryl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5.

In a further embodiment, compounds of Formula I are of the Formula Ia:

(Ia)

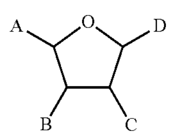

or a pharmaceutically acceptable salt thereof, wherein

A is —$CH_2ONO_2$ or —$CH_2OSO_3H$;

B and C are —OH;

D is

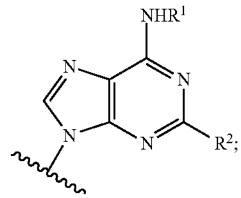

A and B are trans with respect to each other;

B and C are cis with respect to each other;

C and D are cis or trans with respect to each other;

$R^1$ is —$C_3$-$C_8$ monocyclic cycloalkyl, -3- to 7-membered monocyclic heterocycle, or —$C_8$-$C_{12}$ bicyclic cycloalkyl; and $R^2$ is —H or -halo.

In yet another embodiment, compounds of Formula I are of the Formula Ib:

(Ib)

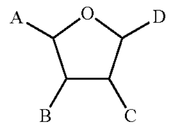

or a pharmaceutically acceptable salt thereof, wherein

A is —$CH_2ONO_2$;

B and C are —OH;

D is

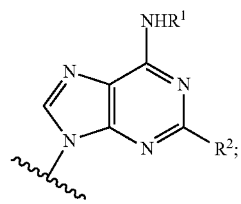

A and B are trans with respect to each other;

B and C are cis with respect to each other;

C and D are cis or trans with respect to each other;

$R^1$ is —$C_3$-$C_8$ monocyclic cycloalkyl, -3- to 7-membered monocyclic heterocycle, or —$C_8$-$C_{12}$ bicyclic cycloalkyl; and $R^2$ is —H or -halo.

In a further embodiment the compound of Formula I is selected from:

Compound A

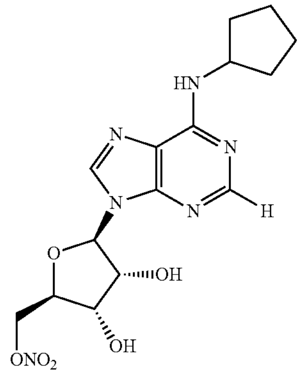

((2R,3S,4R,5R)-5-(6-(cyclopentylamino)-9H-purin-9-yl)-3,4-dihydroxytetrahydrofuran-2-yl)methyl nitrate Compound B

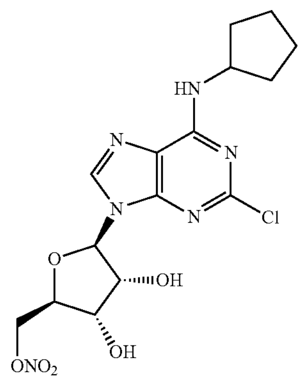

((2R,3S,4R,5R)-5-(2-chloro-6-(cyclopentylamino)-9H-purin-9-yl)-3,4-dihydroxytetrahydrofuran-2-yl) methyl nitrate Compound C

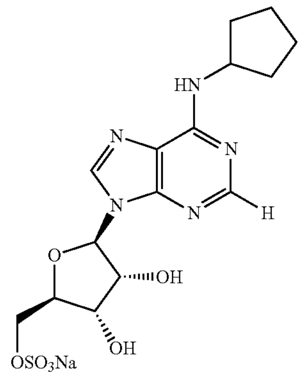

sodium ((2R,3S,4R,5R)-5-(6-(cyclopentylamino)-9H-purin-9-yl)-3,4-dihydroxytetrahydrofuran-2-yl) methyl sulfate Compound D

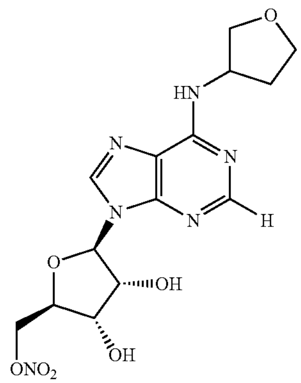

((2R,3S,4R,5R)-3,4-dihydroxy-5-(6-(tetrahydrofuran-3-ylamino)-9H-purin-9-yl)tetrahydrofuran-2-yl) methyl nitrate Compound E

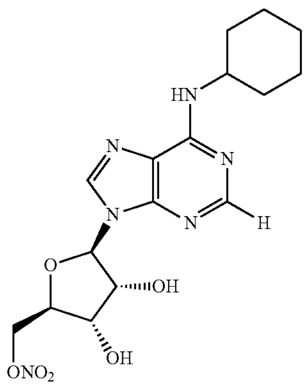

((2R,3S,4R,5R)-5-(6-(cyclohexylamino)-9H-purin-9-yl)-3,4-dihydroxytetrahydrofuran-2-yl)methyl nitrate Compound F

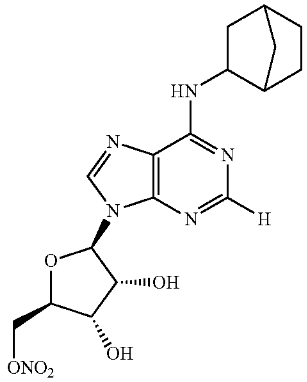

((2R,3S,4R,5R)-5-(6-(bicycle-[2.2.1]-heptan-2-ylamino)-9H-purin-9-yl)-3,4-dihydroxytetrahydrofuran-2-yl)methyl nitrate Compound G

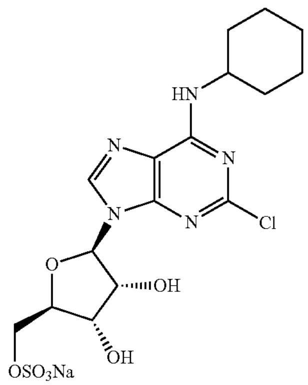

sodium ((2R,3S,4R,5R)-5-(2-chloro-6-(cyclohexylamino)-9H-purin-9-yl)-3,4-dihydroxytetrahydrofuran-2-yl)methyl sulfate Compound H

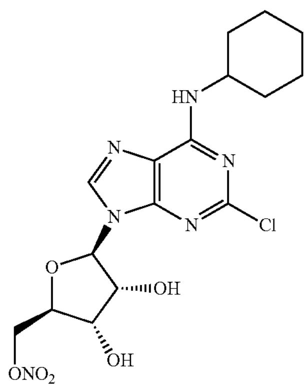

((2R,3S,4R,5R)-5-(2-chloro-6-(cyclohexylamino)-9H-purin-9-yl)-3,4-dihydroxytetrahydrofuran-2-yl) methyl nitrate Compound I

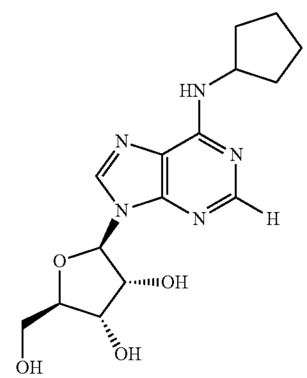

(2R,3R,4S,5R)-2-(6-(cyclopentylamino)-9H-purin-9-yl)-5-(hydroxymethyl)tetrahydrofuran-3,4-diol (N6 Cyclopentyl adenosine (CPA)), and Compound J

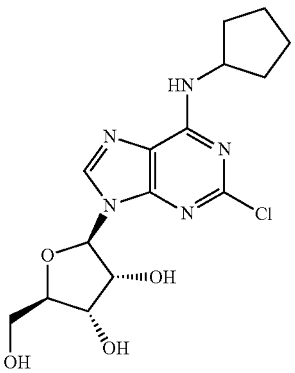

(2R,3R,4S,5R)-2-(2-chloro-6-(cyclopentylamino)-9H-purin-9-yl)-5-(hydroxymethyl)tetrahydrofuran-3,4-diol (N6 Cyclopentyl adenosine (CCPA)), or a pharmaceutically acceptable salt thereof.

In a further embodiment the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, or a pharmaceutically acceptable salt thereof.

In still another embodiment of the ophthalmic combination, the adenosine receptor $A_1$ agonist is Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog Latanoprost.

It may be helpful to provide definitions of certain terms to be used herein. Unless defined otherwise, all technical and scientific terms used herein have the same meaning as is commonly understood by one of skill in the art to which this invention belongs.

The invention provides for a combination of therapeutic agents and administration of the combination of agents to treat elevated intraocular pressure (IOP), as well as conditions caused by elevated IOP. A used herein, a "combination of agents" and similar terms refer to a combination of two types of agents: (1) adenosine receptor $A_1$ agonists (e.g. compounds of Formula I) and/or pharmacologically active metabolites, salts, solvates and racemates of adenosine receptor $A_1$ agonists and (2) prostaglandin analogs (e.g. to latanoprost) and/or pharmacologically active metabolites, salts, solvates and racemates of prostaglandin analogs. Pharmacologically active metabolites include those that are inactive but are converted into pharmacologically active forms in the body after administration.

Administration of the combination includes administration of the combination in a single formulation or unit dosage form, administration of the individual agents of the combination concurrently but separately, or administration of the individual agents of the combination sequentially by any suitable route. The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

An "effective amount" of a combination of agents (e.g. an adenosine receptor $A_1$ agonist and a prostaglandin analog) is an amount sufficient to provide an observable improvement over the baseline clinically observable signs and symptoms of the depressive disorder treated with the combination.

The term "treat" is used herein to mean to relieve, reduce or alleviate at least one symptom of a disease in a subject. For example, in relation to glaucoma, the term "treat" may mean to reduce or alleviate elevated intraocular pressure. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "subject" is intended to include animals, which are capable of suffering from or afflicted with elevated IOP, as well as conditions caused by elevated IOP. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from IOP, or conditions caused by elevated IOP.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

Embodiments of the present invention provide combinations useful for treating reducing and controlling normal or elevated intraocular pressure (IOP) and/or treating glaucoma.

Adenosine is a purine nucleoside that modulates many physiologic processes. Cellular signaling by adenosine occurs through four adenosine receptor subtypes: $A_1$, $A_{2A}$, $A_{2B}$, and $A_3$ as reported by Ralevic and Burnstock (Pharmacol Rev. 50:413-492, 1988) and Fredholm B B et al (Pharmacol Rev. 53:527-552, 2001). In the eye, adenosine $A_1$ receptor agonists lower IOP in mice, rabbits and monkeys (Tian B et al. Exp Eye Res. 64:979-989, 1997; Crosson C E. J Pharmacol Exp Ther. 273: 320-326, 1995; and Avila M Y et al. Br J. Pharmacol. 134:241-245, 2001). While other publications have noted that adenosine A1 receptor agonists in the eye target the conventional outflow pathway via the trabecular meshwork (Husain S et al. J Pharmacol Exp Ther. 320: 258-265, 2007), reduction of IOP via other pathways has not been excluded.

In one embodiment, provided herein is an ophthalmic combination or kit for use in reducing intraocular pressure, comprising i) an adenosine receptor $A_1$ agonist and ii) a prostaglandin analog for use in reducing intraocular pressure in an eye of a subject. In one embodiment the prostaglandin analog is selected from latanoprost, travoprost, unoprostone and bimatoprost. In another embodiment the prostaglandin analog is latanoprost. In another embodiment provided herein the $A_1$ agonist is Compound A. In another embodiment, provided herein is a method of treating normal-tension glaucoma, comprising administering to an affected eye of a subject an effective amount of a combination of Compound A and latanoprost. In another embodiment, provided herein is a method of treating OHT, comprising administering to an affected eye of a subject an effective amount of a combination of Compound A and latanoprost. In another embodiment, provided herein is a method of treating POAG, comprising administering to an affected eye of a subject an effective amount of a combination of Compound A and latanoprost. In one embodiment of the combination, about 0.05 mg/ml to about 7.0 mg/ml of Compound A is applied to an affected eye of a subject from 1 to 4 times daily. In one embodiment, about 20-700 μg of Compound A is applied to an affected eye of a subject from 1 to 4 times daily. In one embodiment, about 20-350 μg of Compound A is applied to an affected eye of a subject from 1 to 4 times daily. The Compound A can be administered in drops, e.g., 1 to 2 drops. In one embodiment about 30 μg/ml to about 50 μg/ml of the prostaglandin is applied to an affected eye. In one embodiment the subject is a human.

It is recognized that compounds of Formula I can contain one or more chiral centers. This invention contemplates all enantiomers, diastereomers, and mixtures of Formulas I thereof.

Furthermore, certain embodiments of the present invention comprise pharmaceutically acceptable salts of compounds according to Formula I. Pharmaceutically acceptable salts comprise, but are not limited to, soluble or dispersible forms of compounds according to Formula I that are suitable for treatment of disease without undue undesirable effects such as allergic reactions or toxicity. Representative pharmaceutically acceptable salts include, but are not limited to, acid addition salts such as acetate, citrate, benzoate, lactate, or phosphate and basic addition salts such as lithium, sodium, potassium, or aluminum.

As used herein, the term "$A_1$ agonist" means an $A_1$ agonist that has an affinity to the $A_1$ receptor while simultaneously having a lower affinity for the $A_2$ and $A_3$ adenosine receptors. Compounds A to J as described herein have affinities to the A1 receptor considerably greater than their respective affinities to the $A_2$A and $A_3$ receptors. The $A_1$ selectivity data for compounds A to J is summarized in the Table below.

| Compound | $A_1$ (Ki (nm)) POTENCY | $A_1 > A_{2A}$ SELECTIVITY [$KiA_2$(nm)/$KiA_1$(nm)] | $A_1 > A_3$ SELECTIVITY [$KiA_3$(nm)/ $KiA_1$(nm)] |
|---|---|---|---|
| Compound A | 0.97 | 4837 | 725 |
| Compound B | 2.63 | 1593 | 195 |
| Compound C | 4.05 | 2250 | 251 |
| Compound D | 10.6 | >9434 | 202 |
| Compound E | 1.32 | 878 | 1098 |
| Compound F | 1.47 | 3945 | 260 |
| Compound G | 1.36 | 200 | 130 |
| Compound H | 8 | 192 | 167 |
| Compound I | 2.3 | 345 | 31.3 |
| Compound J | 0.83 | 2735 | 50 |

Methods that can be used to synthesize these compounds are described below.

The term "$C_1$-$C_{15}$ alkyl" as used herein refers to a straight or branched chain, saturated hydrocarbon having from 1 to 15 carbon atoms. Representative $C_1$-$C_{15}$ alkyl groups include, but are not limited to methyl, ethyl, propyl, isopropyl, butyl, sec-butyl, tert-buty, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl, neodecyl, undecyl, dodecyl, tridecyl, tetradecyl and pentadecyl. In one embodiment, the $C_1$-$C_{15}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{15}$ alkyl is unsubstituted.

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_6$ alkyl" as used herein refers to a straight or branched chain, saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl. Unless indicated, the C1-C6 alkyl is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, 1,3,5-cycloheptatrienyl, cyclooctenyl, 1,3-cyclooctadienyl, 1,4-cyclooctadienyl, 1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkyl is unsubstituted.

The term "$C_8$-$C_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a $C_8$-$C_{12}$ bicyclic cycloalkenyl group, the carbon atom to which the two groups are attached remains tetravalent. Representative $C_8$-$C_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocyclopheptene, decahydroheptalene, octahydroheptalene, hexahydroheptalene, and tetrahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_8$-$C_{12}$ bicyclic cycloalkenyl is unsubstituted.

The term "effective amount" as used herein refers to an amount of a selective adenosine receptor $A_1$ agonist that is effective for: (i) treating or preventing elevated IOP; or (ii) reducing IOP in a human.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—($C_1$-$C_6$ alkyl), —OH, —CN, —COOR', —OC(O)R', —N(R')$_2$, —NHC(O)

$R^{10}$ or —C(O)NHR' groups wherein each R' is independently —H or unsubstituted —$C_1$-$C_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of its ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered monocyclic heterocycles are attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of a the –8- to 12-membered bicyclic heterocycle group can substituted with one or more of the following groups: -halo, —O—($C_1$-$C_6$ alkyl), —OH, —CN, —COOR', —OC(O)R', —$N(R')_2$, —NHC(O)R'. or —C(O)NHR' groups wherein each R' is independently —H or unsubstituted —$C_1$-$C_6$ alkyl. Unless indicated, the 8- to 12-membered bicyclic heterocycle is unsubstituted. Representative examples of a "phenylene group" are depicted below:

The phrase "pharmaceutically acceptable salt," as used herein, is a salt of an acid and a basic nitrogen atom of a purine compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a purine compound having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a purine compound. Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached.

The term "subject" as used herein is a mammal, e.g., a human, mouse, rat, guinea pig, dog, cat, horse, cow, pig, or non-human primate, such as a monkey, chimpanzee or baboon. In one embodiment, the monkey is a Cynomolgus monkey. In one embodiment, the subject is a human.

The term "treat," "treated," "treating" or "treatment" includes the diminishment or alleviation of at least one symptom associated or caused by the state, disorder or disease being treated. In certain embodiments, the treatment comprises the induction of elevated IOP, followed by the activation of the compound of the invention, which would in turn diminish or alleviate at least one symptom associated or caused by the elevated IOP. For example, treatment can be diminishment of one or several symptoms of a disorder or complete eradication of a disorder.

The term "use" includes any one or more of the following embodiments of the invention, respectively: the use in the treatment of elevated IOP; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from glaucoma, POAG or OHT.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

As used herein, the term "drop" or "drops" refers to a quantity of ophthalmically acceptable fluid that resembles a liquid drop. In one embodiment, a drop refers to a liquid volume equivalent to about 5 μl to about 200 e.g., about 30 μl to about 80 μl. refers to a liquid volume equivalent to about 5 μl to about 200 μl, e.g., about 30 μl to about 80 μl.

The following abbreviations are used herein and have the indicated definitions: CCPA is 2-chloro-N-6-cyclopentyladenosine; CPA is N6-cyclopentyladenosine; NECA is adenosine-5'-(N-ethyl)carboxamido; NMR is nuclear magnetic resonance; R-PIA is N6-(2-phenyl-isopropyl) adenosine, R-isomer; OHT is ocular hypertension or POAG is primary open-angle glaucoma; HPβCD is hydroxypropyl β-cyclodextrin.

Dosages

The optimal dose of the combination of agents for treatment of elevated IOP can be determined empirically for each individual using known methods and will depend upon a variety of factors, including, though not limited to, the degree of advancement of the disease; the age, body weight, general health, gender and diet of the individual; the time of administration; and other medications the individual is taking. Optimal dosages may be established using routine testing and procedures that are well known in the art. Daily dosages for the compounds of formula I can be 10 μg to about 2000 μg.

The amount of combination of agents that may be combined with the carrier materials to produce a dosage form will vary depending upon the individual treated.

Frequency of dosage may vary depending on the compound used and the particular elevated IOP condition to be treated or prevented and the patient's/subject's medical history. In general, the use of the minimum dosage that is sufficient to provide effective therapy is preferred. Patients may generally be monitored for therapeutic effectiveness using assays or tests suitable for the IOP condition being treated or prevented, which will be familiar to those of ordinary skill in the art.

The dosage form can be prepared by various conventional mixing, comminution and fabrication techniques readily apparent to those skilled in the chemistry of drug formulations.

The drug compounds of the present invention (for example, a compound of formula (I), particularly compound A, and a prostaglandin analog, e.g., latanoprost) are present in the combinations, dosage forms, pharmaceutical compositions and pharmaceutical formulations disclosed herein in a ratio in the range of 100:1 to 1:100, more preferably 1:10-1:100, e.g., 1: 15-1:60, e.g., 1:20-1:50 (prostaglandin analog:$A_1$ agonist).

The optimum ratios, individual and combined dosages, and concentrations of the drug compounds that yield efficacy without toxicity are based on the kinetics of the active ingredients' availability to target sites, and are determined using methods known to those of skill in the art.

Pharmaceutical Compositions

The pharmaceutical compositions or combinations provided herein (e.g., a compound of formula (I), particularly compound A, and a prostaglandin analog, e.g., latanoprost) can be tested in clinical studies. Suitable clinical studies may be, for example, open label, dose escalation studies in patients with elevated IOP. The beneficial effects on elevated IOP may be determined directly through the results of these studies which are known as such to a person skilled in the art. Such studies may be, in particular, suitable to compare the effects of a monotherapy using the active ingredients and a combination of the invention. In one embodiment, the dose of a compound of formula (I), e.g., compound A, is escalated until the Maximum Tolerated Dosage is reached, and a prostaglandin analog is administered with a fixed dose. Alternatively, a compound of formula (I), e.g., compound A, may be administered in a fixed dose and the dose of the prostaglandin analog may be escalated. Each patient may receive doses of a compound of formula (I), e.g., compound A, either daily, or twice-four times daily. The efficacy of the treatment may be determined in such studies, e.g., after 12, 18 or 24 weeks by evaluation of symptom scores every 6 weeks.

The administration of a pharmaceutical combination of the invention may result not only in a beneficial effect, e.g. with regard to alleviating, delaying progression of or inhibiting the symptoms elevated IOP, but also in further surprising beneficial effects, e.g. fewer side-effects or an improved quality of life, compared with a monotherapy applying only one of the pharmaceutically active ingredients used in the combination of the invention.

A further benefit may be that lower doses of the active ingredients of the combination of the invention may be used, for example, that the dosages need not only often be smaller but may also be applied less frequently, which may diminish the incidence or severity of side-effects. This is in accordance with the desires and requirements of the patients to be treated.

It is one objective of this invention to provide a pharmaceutical composition comprising a quantity, which may be jointly therapeutically effective at reducing IOP and/or reducing glaucoma. In this composition, a compound of formula (I) and a prostaglandin analog may be administered together, one after the other or separately in one combined unit dosage form or in two separate unit dosage forms.

The pharmaceutical compositions for separate administration of both compounds, may be prepared in a manlier known per se and are those suitable for topical ocular administration to mammals (warm-blooded animals), including humans, comprising a therapeutically effective amount of at least one pharmacologically active combination partner alone, e.g. as indicated above, or in combination with one or more pharmaceutically acceptable carriers or diluents.

Formulations

The drug combinations provided herein may be formulated by a variety of methods apparent to those of skill in the art of pharmaceutical formulation. Suitable pharmaceutical formulations may contain, for example, from about 0.1% to about 99.9%, preferably from about 1% to about 60%, of the active ingredient(s). It will be appreciated that the unit content of a combination partner contained in an individual dose of each dosage form need not in itself constitute an effective amount since the necessary effective amount may be reached by administration of a plurality of dosage units.

In particular, a therapeutically effective amount of each of the combination partner of the combination of the invention may be administered simultaneously or sequentially and in any order. For example, the method of reducing IOP according to the invention may comprise (i) administration of the first agent (a) in free or pharmaceutically acceptable salt form and (ii) administration of an agent (b) in free or pharmaceutically acceptable salt form, simultaneously or sequentially in any order, in jointly therapeutically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the condition being treated, the severity of the condition being treated. Thus, the dosage regimen of the combination of the invention is selected in accordance with a variety of factors including the medical history of the patient. A clinician or physician of ordinary skill can readily determine and prescribe the effective amount of the single active ingredients required to alleviate, counter or arrest the progress of the condition.

The compounds according to formula I can be incorporated into various types of ophthalmic compositions or formulations for delivery. Formula I compounds may be delivered directly to the eye (for example: topical ocular drops or ointments; slow release devices such as pharmaceutical drug delivery sponges implanted in the cul-de-sac or implanted adjacent to the sclera or within the eye; periocular, conjunctival, sub-tenons, intracameral, intravitreal, or intracanalicular injections) using techniques well known by those of ordinary skill in the art. It is further contemplated that the agents of the invention may be formulated in intraocular insert or implant devices.

The compounds of Formula I are preferably incorporated into topical ophthalmic formulations with a pH of about 4-8 for delivery to the eye. One such formulation is an aqueous suspension formulation described in detail in PCT/US2010/054040, and outlined below in the examples. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity or solubility such as hydroxypropyl β-Cyclodextrin (HPβCD), hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient may be combined with a preservative in an appropriate vehicle such as mineral oil, liquid lanolin, or white petrolatum. Sterile ophthalmic gel formulations may be prepared by suspending the compound in a hydrophilic base prepared from the combination of, for example, carbopol-974, or the like, according to the published formulations for analogous ophthalmic preparations; preservatives and tonicity agents can be incorporated.

Compounds in preferred embodiments are contained in a composition in amounts sufficient to lower IOP in patients experiencing elevated IOP and/or maintaining normal IOP levels in POAG or OHT patients. Such amounts are referred to herein as "an amount effective to control or reduce IOP," or more simply "an effective amount." The compounds will normally be contained in these formulations in an amount 0.05 mg/ml to 7.0 mg/ml but preferably in an amount of 0.4 to 7.0 mg/ml. Thus, for topical presentation 1 to 2 drops of these formulations would be delivered to the surface of the eye from 1 to 4 times per day, according to the discretion of a skilled clinician.

Methods of Synthesis

Compounds according to Formula I can be prepared by using synthetic procedures described in U.S. Pat. No. 7,423,144, the disclosure of which is incorporated herein in its entirety, as well as other published methods (see Cristalli et al., *J. Med. Chem.* 35:2363-2369, 1992; Cristalli et al., *J. Med. Chem.* 37:1720-1726, 1994; Cristalli et al, *J. Med. Chem.* 38:1462-1472, 1995; and Camaioni et al., *Bioorg. Med. Chem.* 5:2267-2275, 1997), or by using the synthetic procedures outlined below.

Scheme 1 shows methods for making nucleoside intermediates that are useful for making the compounds of the invention.

Scheme 1

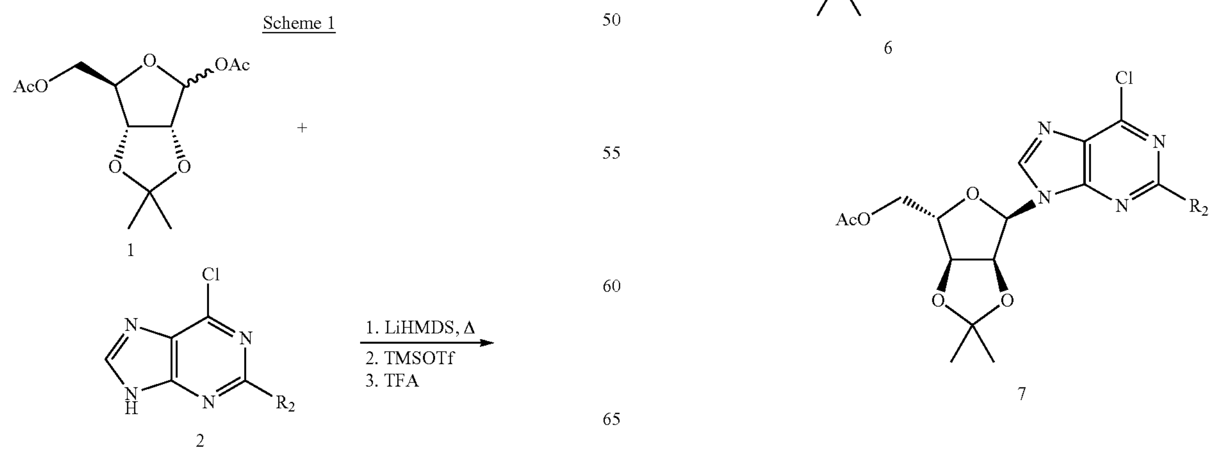

-continued wherein $R_2$ is as defined above.

The protected ribose compound of Formula 1 can be coupled with a purine compound of Formula 2 using lithium hexamethyldisilazide and trimethylsilyl triflate, followed by acetonide removal using trifluoroacetic acid to provide nucleoside intermediates of Formula 3 and their corresponding other anomers of Formula 4. Similarly, the ribose diacetate of Formula 5 can be coupled with a compound of Formula 2 using lithium hexamethyldisilazide and trimethylsilyl triflate to provide acetonide-protected nucleoside intermediates of Formula 6 and their corresponding other anomers of Formula 7.

Scheme 2 shows a method useful for making the adenosine intermediates of Formula 8 which are useful for making the compounds of the invention.

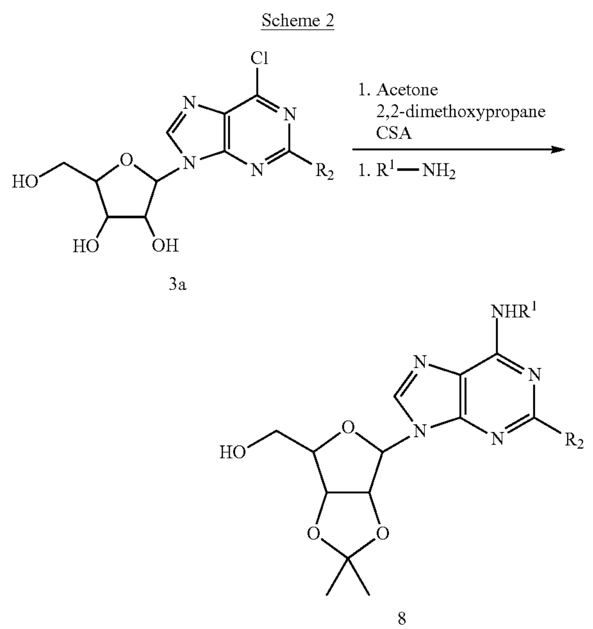

where $R^1$ and $R^2$ are defined above.

The 6-chloroadenosine derivative of formula 3a is converted to its 2',3'-acetonide using acetone and 2,2-dimethoxypropane in the presence of camphorsulfonic acid. The acetonide can be further derivatized using an amine of formula R'—$NH_2$ in the presence of base to provide compounds of formula 8.

Methodology useful for making other compounds of the invention is described in Scheme 4.

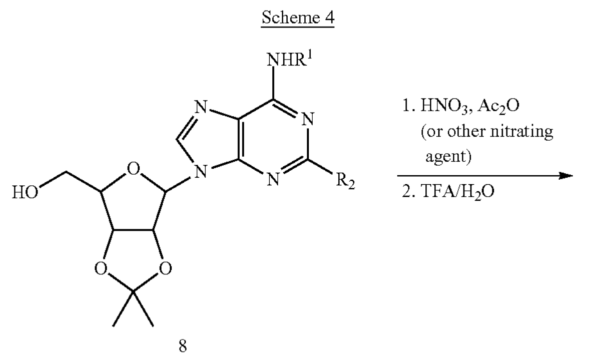

-continued

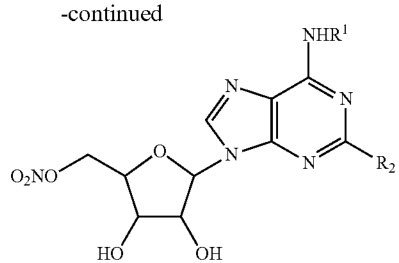

where $R^1$ and $R^2$ are defined above.

The adenosine intermediates of formula 8 can be converted to their 5'-nitrate analogs using nitric acid in the presence of acetic anhydride, or other nitrating agents, such as MsCl/$ONO_3$ or nitrosonium tetrafluoroborate. Acetonide removal using TFA/water provides compounds of the invention.

Methodology useful for making the Purine Derivatives of Formula (Id) wherein $R^3$ is —$CH_2OSO_3H$ is outlined in Scheme 6.

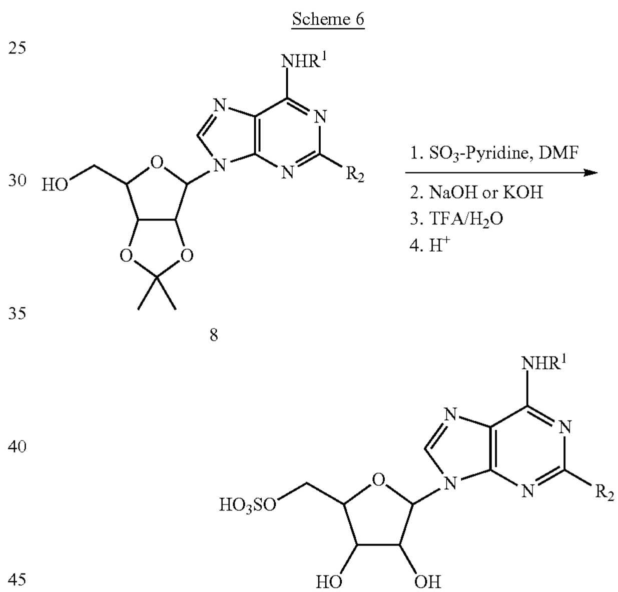

where $R^1$ and $R^2$ are defined above.

The adenosine intermediates of formula 8 can be treated with sulfur trioxide-pyridine complex to provide the corresponding 5'-sulfonic acid pyridine salt intermediate. The pyridine salt intermediate can then be neutralized using NaOH or KOH, followed by acetonide removal using TFA/water to provide the corresponding sodium or potassium salt, respectively, of the Purine Derivatives of Formula (Id) wherein A is —$CH_2OSO_3H$. Treatment of the sodium or potassium salt with strong aqueous acid, such as sulfuric or hydrochloric acid, provides compounds of the invention wherein A is —$CH_2OSO_3H$.

EXAMPLES/EXPERIMENTAL

The experiments were conducted in ten conscious cynomolgus monkeys (*Macaca fascicularis*). The monkeys were without ocular disease and had intraocular pressure readings in the normal range, and were classed as normotensive monkeys. Prior to the study, the monkeys were previously acclimated to the study procedures (e.g., dosing, tonometry, ocular examinations, and handling), and allowed a washout period before each treatment.

Compound A was administered in two different formulations:

1. HPβCD (hydroxypropyl-β-cyclodextrin) Formulation

In one formulation, lyophilized Compound A to HPβCD in 1:20 (wt/wt) was reconstituted with 0.9% Saline for Injection, USP.

2. Aqueous Suspension Formulation

The aqueous formulation comprised of the following:

| Ingredient | %, w/v |
|---|---|
| Compound A, micronized | 2.0 |
| Sodium CMC, low viscosity | 0.7 |
| Benzalkonium Chloride | 0.01 |
| Polysorbate 80 | 0.3 |
| Citric Acid Monohydrate | 0.15 (7 mM) |
| NaCl | 0.8% (qs to 290-300 mOsm) |
| NaOH/HCl (pH adjustment) | pH 5.1 ± 0.1 |
| Purified Water | q.s. 100 |

Treatment 1

In the first treatment, 10 monkeys received topically 100 mcg of Compound A at 40 mcL, formulated in an aqueous suspension in one study eye and vehicle/placebo control applied topically in the contralateral eye. During the study, the intraocular pressures (IOP) of both the study eye and contralateral eye were measured repeatedly using a calibrated pneumotonometer following an application of a topical anesthetic (proparacaine). The control in the first treatment was a 40 mcL composition of 0.8% sodium chloride (NaCl), 0.15% citrate, 0.01% benzalkonium chloride, 0.3% polysorbate 80, and 0.7% sodium (Na) carboxymethylcellulose.

Treatment 2

In the second treatment, 10 monkeys received latanoprost (Xalatan™) topically dosed via 2 drops at 15 mcL apart (at a concentration of 50 mcg/mL) for a total dose of 1.5 mcg in one study eye and immediately after received an additional topical dose of 500 mcg of Compound A at 40 mcL formulated in an HPβCD solution in one study eye and vehicle/placebo of HPβCD in saline in the contralateral eye.

Treatment 3

In the third treatment, 10 monkeys received latanoprost (Xalatan™) dosed via 2 drops at 15 mcL apart (at a concentration of 50 mcg/mL) for a total dose of 1.5 mcg in one study eye and 2 drops of saline vehicle in the contralateral eye. This treatment was performed at two separate times with a sufficient washout between treatments. The IOPs of both the study eye and contralateral eye were measured repeatedly using a calibrated pneumotonometer following an application of a topical anesthetic (proparacaine).

Treatment 4

In the fourth treatment, 10 monkeys received latanoprost (Xalatan™) topically dosed via 2 drops at 15 mcL apart (at a concentration of 50 mcg/mL) for a total dose of 1.5 mcg in one study eye and saline in the contralateral eye. Approximately 4 hours later, the monkeys received the additional topical dose of 100 mcg of Compound A at 40 mcL formulated in an aqueous suspension in the same study eye and vehicle/placebo of 0.8% sodium chloride (NaCl), 0.15% citrate, 0.01% benzalkonium chloride, 0.3% polysorbate 80, and 0.7% sodium (Na) carboxymethylcellulose topically in the contralateral eye. The intraocular pressures (IOP) of both the study eye and contralateral eye were measured repeatedly using a calibrated pneumotonometer following an application of a topical anesthetic (proparacaine).

Treatment 5

In the fifth treatment, 10 monkeys received latanoprost (Xalatan™) topically dosed via 2 drops at 15 mcL apart (at a concentration of 50 mcg/mL) for a total dose of 1.5 mcg in one study eye and saline in the contralateral eye. Approximately 5 hours later, the monkeys received the additional topical dose of 100 mcg of Compound A at 40 mcL formulated in an aqueous suspension in the same study eye and vehicle/placebo of 0.8% sodium chloride (NaCl), 0.15% citrate, 0.01% benzalkonium chloride, 0.3% polysorbate 80, and 0.7% sodium (Na) carboxymethylcellulose applied topically in the contralateral eye. The IOPs of both the study eye and contralateral eye were measured repeatedly using a calibrated pneumotonometer following an application of a topical anesthetic (proparacaine).

Results

Figure 2:
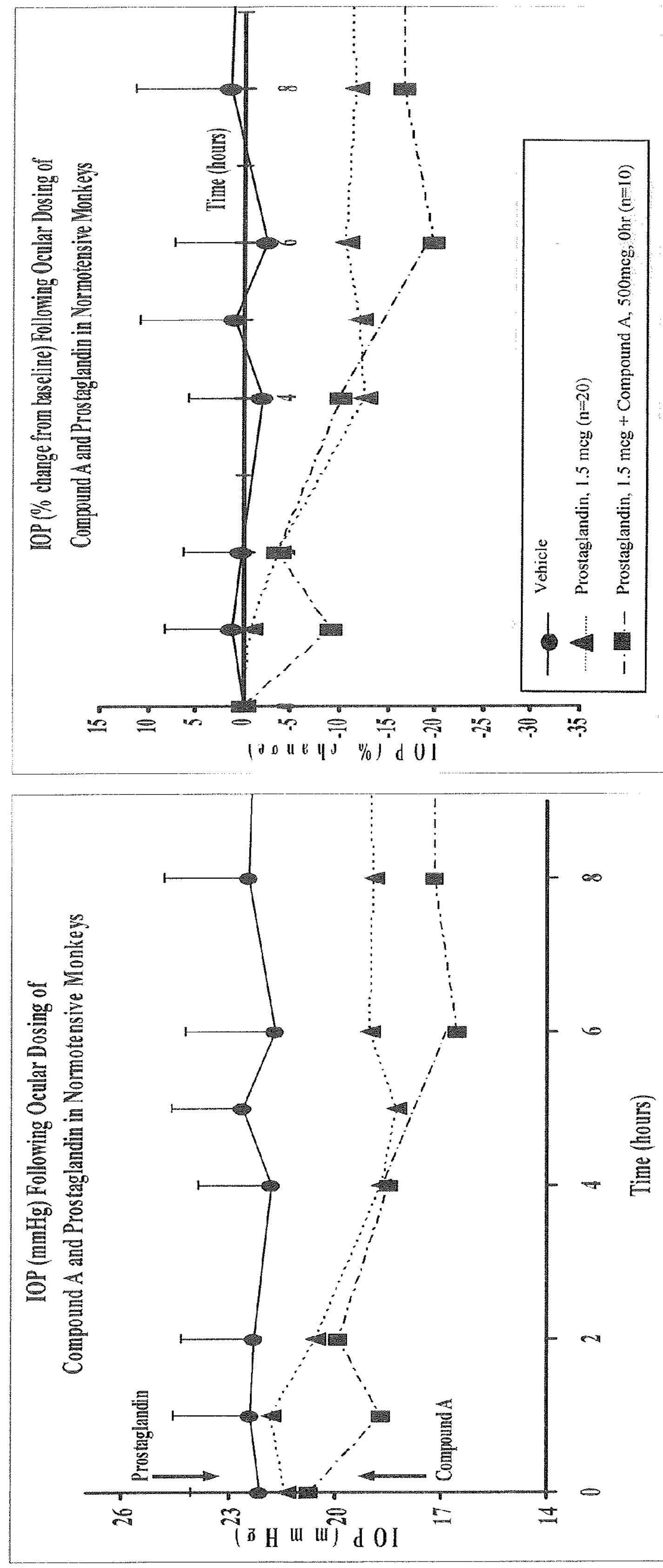
FIG. 2: shows the reduction in IOP (% change from baseline) in normotensive monkeys following ocular dosing of 100 mcg or Compound A at 4 hrs after ocular dosing of a prostaglandin analog compared to the reduction in IOP following dosing of a prostaglandin analog alone.

The results from the treatments are illustrated in FIGS. 1 through 4. The results of Treatment 1 can be seen in FIG. 1, Treatments 2 and 3 in FIG. 2, Treatments 3 and 4 in FIG. 3 and Treatments 3 and 5 in FIG. 4. It can be seen from the plots in FIG. 1 that show the reduction of IOP in (mmHg and % change from baseline) following ocular dosing of 100 mcg of an aqueous suspension of Compound A. The plots in FIG. 2 show the reduction of IOP in (mmHg and % change from baseline) following the simultaneous ocular dosing of 500 mcg of an HPβCD suspension of Compound A and 1.5 mcg of prostaglandin relative to the reduction of IOP seen with the ocular dosing of 1.5 mcg of prostaglandin alone.

Figure 3:
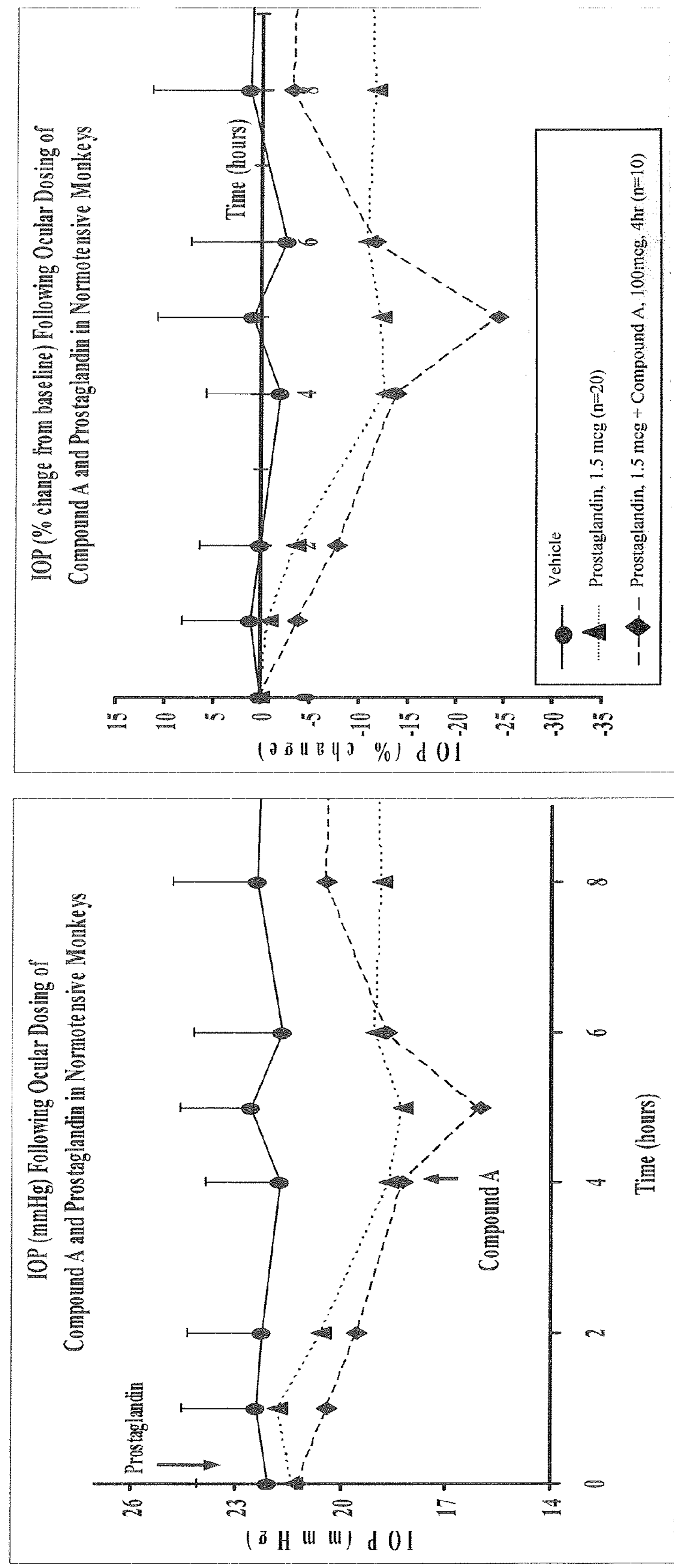
FIG. 3: shows the reduction in IOP (mmHg) in normotensive monkeys following (i) ocular dosing of Compound A at 4 hrs after ocular dosing of a prostaglandin analog compared to the reduction in IOP following dosing of a prostaglandin analog alone and (ii) ocular dosing of 500 mcg Compound A immediately after ocular dosing of a prostaglandin analog compared to the reduction in IOP following dosing of a prostaglandin analog alone FIG. **4*a***: shows the reduction in IOP (% change from baseline) in normotensive monkeys following (i) ocular dosing of Compound A at 4 hrs after ocular dosing of a prostaglandin analog compared to the reduction in IOP following dosing of a prostaglandin analog alone and (ii) ocular dosing of 500 mcg Compound A immediately after ocular dosing of a prostaglandin analog compared to the reduction in IOP following dosing of a prostaglandin analog alone.
Figure 4:
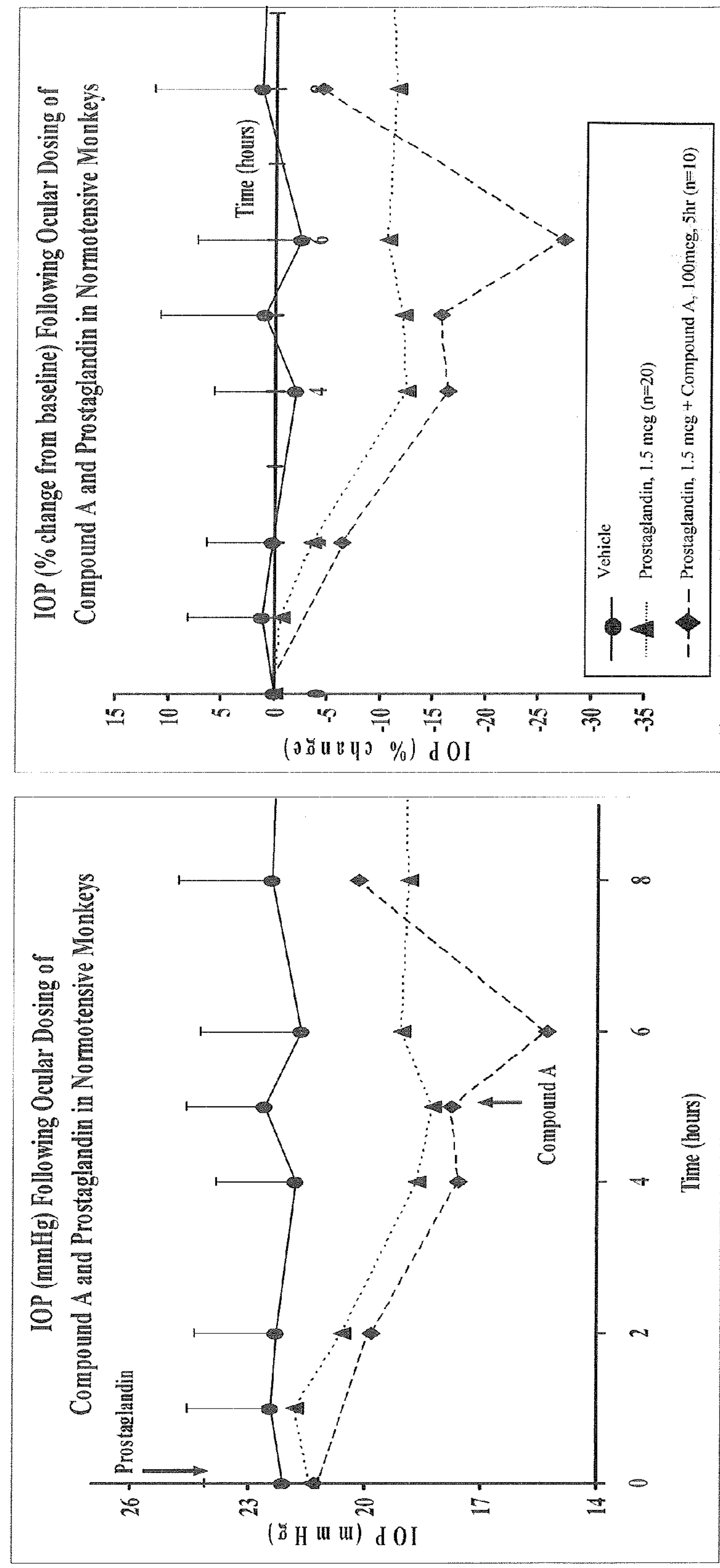

The plots in FIG. 3 show the reduction of IOP in (mmHg and % change from baseline) following the ocular dosing of 100 mcg of an aqueous suspension of Compound A given 4 hours after the ocular dosing of 1.5 mcg of prostaglandin relative to the reduction of IOP seen with ocular dosing of 1.5 mcg of prostaglandin alone. The plots in FIG. 4 show the reduction of IOP in (mmHg and % change from baseline) following the ocular dosing of 100 mcg of an aqueous suspension of Compound A given 5 hours after the ocular dosing of 1.5 mcg of prostaglandin relative to the reduction of IOP seen with ocular dosing of 1.5 mcg of prostaglandin alone. It can be recognized from FIGS. 2 to 4 that two different doses of Compound. A were administered and Compound A was also administered simultaneously with latanoprost and subsequent to the administration of latanoprost at two different times. In each arm of the study, a further significant reduction in IOP was observed 1 hour after the administration of Compound A relative to the IOP of the administration of latanoprost alone.

Multidose Study

A multi-dose study was conducted to evaluate the IOP lowering effect of twice-daily topical administration of Compound A in a suspension formulation in combination with once daily topical Latanoprost administration in conscious cynomolgus monkeys. Animals received latanoprost for approximately 2 weeks prior to the combination treatment with Compound A. IOP was routinely monitored beginning prior to the treatment through the combination treatments.

A suspension formulation of 1.625 mg/mL Compound A was formulated in 0.7% sodium carboxymethyl cellulose (CMC), 0.3% polysorbate 80, 0.01% benzalkonium chloride, 0.15% citric acid, and 0.8% sodium chloride (NaCl). The placebo contained these same ingredients, except for Compound A. Latanoprost (0.05 mg/mL) was dosed as supplied commercially. Ten female, ocular normotensive cynomolgus monkeys (*Macaca fascicularis*), aged 3 to 4 years old at initiation of treatment, were acclimated to ocular topical dosing and repeated IOP measurements using a pneumatonometer (Model 30 Classic) without general anesthesia or sedation (conscious) and dosed as indicated in Table 1.

TABLE 1

| Doses and Treatment Regimen | | | | | | |
|---|---|---|---|---|---|---|
| Duration | Treatment Right Eye[a] | Dose Concentration (mg/mL) | Dose Level Right Eye (μg/dose/eye) | Treatment Left Eye[b] | Dose Level Left Eye | Dose Volume (No. of drops/volume [μL/drop]) |
| 2 weeks | Latanoprost (QD) | 0.05 | 1.5 | BSS (QD) | 0 | 2/15 |
| 1 week | Latanoprost (QD) | 0.05 | 1.5 | BSS (QD) | 0 | 2/15 |
| | Compound A Suspension Formulation (BID) | 1.625 | 65 | Placebo Control (bid) | 0 | 1/40 |

QD = Once each day.

BID = Twice each day.

BSS = Balanced salt solution.

[a]For the right eyes, Latanoprost was dosed once daily starting approximately 2 weeks prior to the combination treatment; the drug was administered via two drops (1.5 μg) approximately 1 minute apart. For the combination, Compound A was dosed as a single drop at 65 μg/dose BID (for a total dose of 130 μg/day) approximately 5 hours apart.

[b]For the left eyes, respective matching controls, balanced salt solution (BSS) for latanoprost and Placebo for Compound A. The volumes and regimen were similar to that of treated right eyes.

Figure 5:
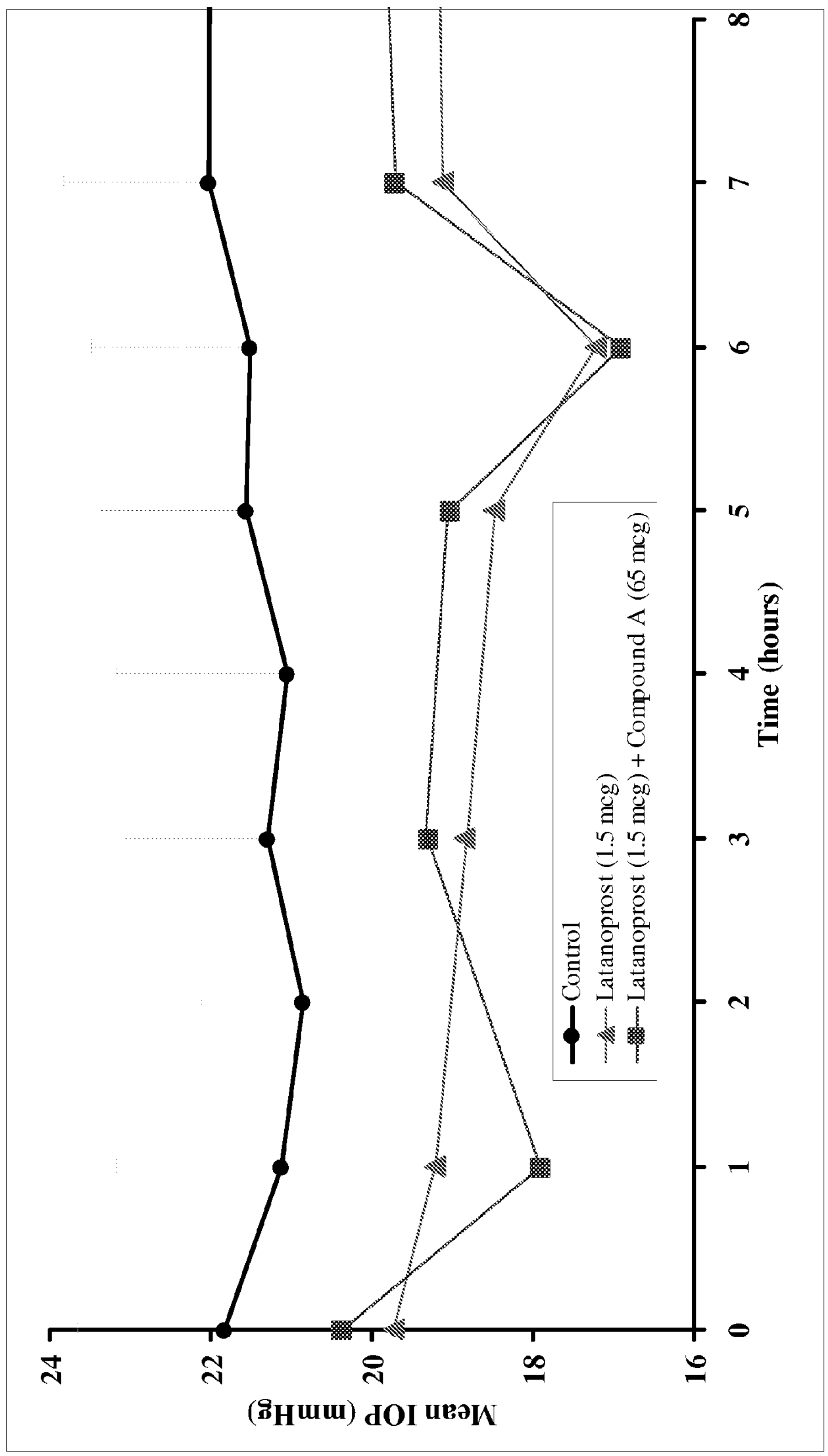
FIG. 5: shows mean IOP (mm Hg) of treated right eye of normotensive monkeys (n=10) after repeated twice daily topical administration of Compound A (65 μg/dose; 130 mg/day) to the right eye following once daily topical dose of Latanoprost (1.5 μg/dose) to the right eye. The combination treatment is compared to the mean IOP following repeated once daily topical administration of Latanoprost (1.5 μg/dose) alone to the right eye. The left eye received controls (balanced salt solution for latanoprost and placebo for Compound A) as the same volume as the right eye. Plots show mean IOP values measured over several days.
Figure 6:
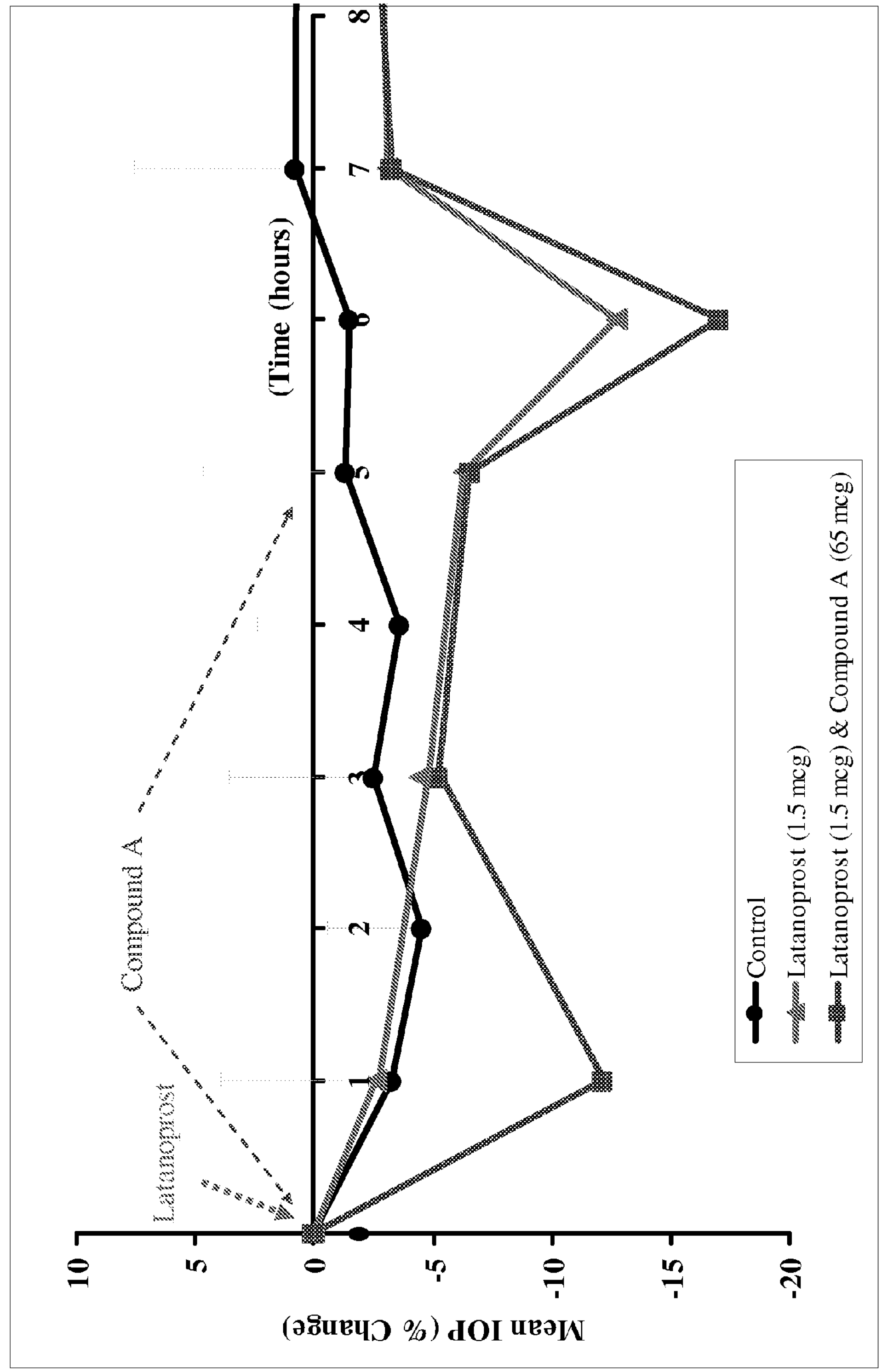
FIG. 6: shows mean percentage change in IOP from baseline of treated right eye of normotensive monkeys (n=10) after twice daily topical administration of Compound A (65 μg/dose; 130 μg/day) to the right eye following once daily topical dose of Latanoprost (1.5 μg/dose) to the right eye. The combination treatment is compared to the mean percentage change in IOP from baseline following repeated once daily topical administration of Latanoprost (1.5 μg/dose) alone to the right eye. The left eye received controls (balanced salt solution for latanoprost and placebo for Compound A) as the same volume as the right eye. Plots show mean percentage change from baseline of IOP measured over several days.

Intraocular pressure was measured from both eyes (three readings/eye/time interval with mean values represented in the data tables) beginning approximately 1 hour predose, at Time 0 (just prior to dosing), and after dosing at various time intervals. Mean IOP values and the percent change in IOP levels from the baseline level were calculated. The FIGS. 5 and 6 show summarized data from this phase of the study of the combined IOP mean values of treatments and standard deviation of the mean for the control. The control plot includes the combined mean values of all treatments (BSS alone and BSS in combination with Placebo). The mean IOP levels in the control eye ranged from 21 to 22 mmHg.

Results

Effect of Repeated Once Daily Topical Administration of Latanoprost on IOP

FIG. 5 shows mean IOP (mm Hg) and FIG. 6 shows mean percentage change in IOP from baseline of four separate lop measurement sessions after repeated once daily topical administration of latanoprost to the right eyes of normotensive monkeys. The mean IOP levels were reduced to about 2 mm Hg at peak trough in the treated eyes. This correlated to approximately 13% reduction from the mean IOP baseline levels. After repeated treatments with latanoprost for two weeks, the IOP of treated eyes was slightly lower than that of the control eyes including at pre-dose times.

Effect of Twice Daily Topical Administration of Compound A in a Suspension Formulation (65 μg Compound A/dose) in Combination with Once Daily Topical Latanoprost on IOP after Establishment of Steady State IOP Levels with Daily Topical Latanoprost FIG. 5 shows mean IOP (mm Hg) and 6 shows mean percentage change in IOP from baseline of three IOP measurement sessions of treated right eyes in normotensive monkeys following repeated daily topical administration. Compound A (65 μg/close/eye; 130 μg/eye/day) was delivered twice daily to the right eyes following once daily topical doses of latanoprost (1.5 μg/dose) to the right eyes.

After establishment of steady state IOP levels with daily topical latanoprost for approximately two weeks, the right eye received repeated twice daily treatment of Compound A (65 μg/dose, 130 μg/day) in combination with once daily latanoprost (1.5 μg/eye). The combination treatment showed a greater reduction in IOP compared with that of latanoprost alone at 1 hour after each of the twice daily dose (at Time 0 and 5 hours) of Compound A. Topical administrations of Compound A caused a rapid reduction in IOP compared to the IOP level established by daily topical latanoprost administration. IOP was reduced to a greater extent with the combination treatment than that observed with latanoprost alone. At peak troughs, IOP was reduced to approximately 12% and 17% after the first and second daily doses, respectively. This trend was consistent in each IOP session of the combination treatment.

It is anticipated that results of a similar or more significant extent would be observed with further pre-clinical studies in hypertensive monkeys and would similarly extend to other mammals including humans.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to combinations, kits, compounds, means, methods, and/or steps disclosed herein.

The invention claimed is:

1. A method of reducing intraocular pressure (IOP) and associated diseases and conditions caused by elevated IOP in a subject in need thereof by administering to an affected eye of the subject, an effective amount of:

(i) an adenosine receptor $A_1$ agonist compound of Formula (I)

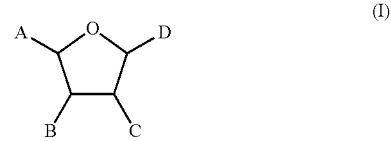

(I)

or a pharmaceutically acceptable salt thereof, wherein

A is —$CH_2OH$, —$CH_2ONO_2$ or —$CH_2OSO_3H$;

B and C are —OH;

D is

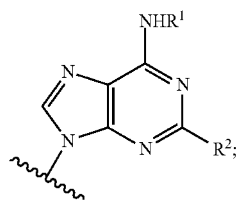

A and B are trans with respect to each other;

B and C are cis with respect to each other;

C and D are cis or trans with respect to each other;

$R^1$ is —H, —$C_1$-$C_{10}$ alkyl, -aryl, -3- to 7-membered monocyclic heterocyclyl, -8- to 12-membered bicyclic heterocyclyl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;

$R^2$ is —H, halo, —CN, —$NHR^4$, —NHC(O)$R^4$, —NHC(O)O$R^4$, —NHC(O)NH$R^4$, —NHNHC(O)$R^4$, —NHNHC(O)O$R^4$, —NHNHC(O)NH$R^4$, or —NH—N=C($R^6$)$R^7$;

$R^4$ is —$C_1$-$C_{15}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;

$R^6$ is —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)$—COO—($C_1$-$C_{10}$ alkyl);

$R^7$ is —H, —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5, and (ii) the prostaglandin analog, latanoprost.

2. The method of claim 1, wherein the diseases and conditions caused by elevated IOP in a human are selected from the group consisting of normal-tension glaucoma, ocular hypertension (OHT), and primary open-angle glaucoma (POAG).

3. The method according to claim 1 wherein the $A_1$ receptor agonist compound is applied to an eye of the subject in need thereof, simultaneously, separately or sequentially to the application of the prostaglandin analog, latanoprost, to the eye of the subject.

4. The method according to claim 1 wherein the $A_1$ receptor agonist compound is applied to an eye of the subject in need thereof, simultaneously to the application of the prostaglandin analog, latanoprost, to the eye of the subject.

5. The method according to claim 1 wherein the $A_1$ receptor agonist compound is applied to an eye of the subject in need thereof, sequentially to the application of the prostaglandin analog, latanoprost, to the eye of the subject.

6. The method according to claim 1 wherein the compound of Formula (I) is selected from the group consisting of:

Compound A

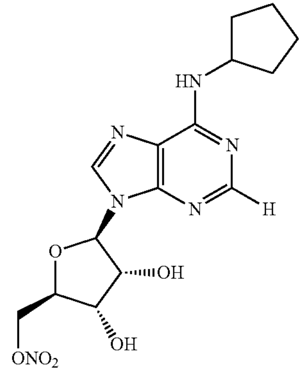

((2R,3S,4R,5R)-5-(6-(cyclopentylamino)-9H-purin-9-yl)-3,4-dihydroxytetrahydrofuran-2-yl)methyl nitrate, Compound B

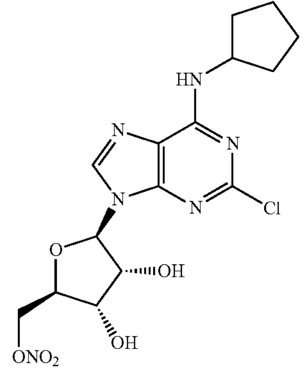

((2R,3S,4R,5R)-5-(2-chloro-6-(cyclopentylamino)-9H-purin-9-yl)-3,4-dihydroxytetrahydrofuran-2-yl)methyl nitrate, Compound C

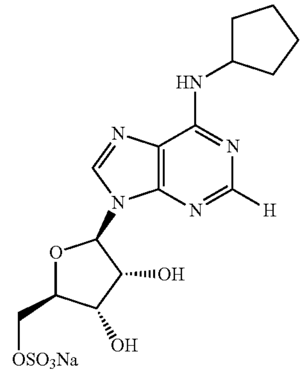

sodium ((2R,3S,4R,5R)-5-(6-(cyclopentylamino)-9H-purin-9-yl)-3,4-dihydroxytetrahydrofuran-2-yl)methyl sulfate, Compound D

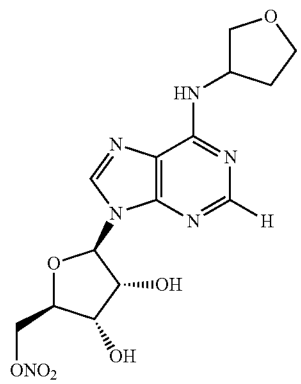

((2R,3S,4R,5R)-3,4-dihydroxy-5-(6-(tetrahydrofuran-3-ylamino)-9H-purin-9-yl)tetrahydrofuran-2-yl)methyl nitrate, Compound E

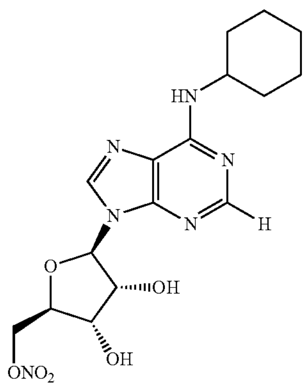

((2R,3S,4R,5R)-5-(6-(cyclohexylamino)-9H-purin-9-yl)-3,4-dihydroxytetrahydrofuran-2-yl)methyl nitrate, Compound F

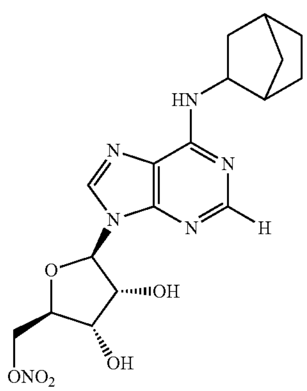

((2R,3S,4R,5R)-5-(6-(bicycle-[2.2.1]-heptan-2-ylamino)-9H-purin-9-yl)-3,4-dihydroxytetrahydrofuran-2-yl) methyl nitrate, Compound G

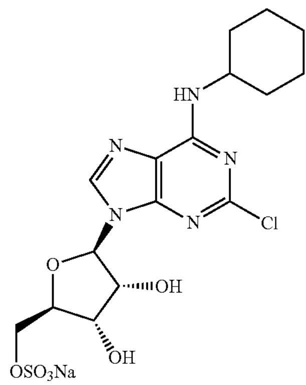

sodium ((2R,3S,4R,5R)-5-(2-chloro-6-(cyclohexylamino)-9H-purin-9-yl)-3,4-dihydroxytetrahydrofuran-2-yl)methyl sulfate, Compound H

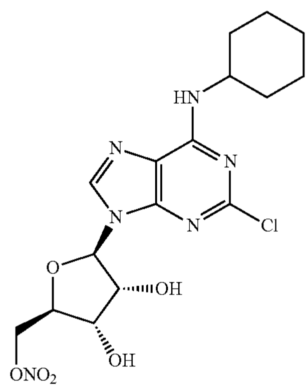

((2R,3S,4R,5R)-5-(2-chloro-6-(cyclohexylamino)-9H-purin-9-yl)-3,4-dihydroxytetrahydrofuran-2-yl)methyl nitrate Compound I

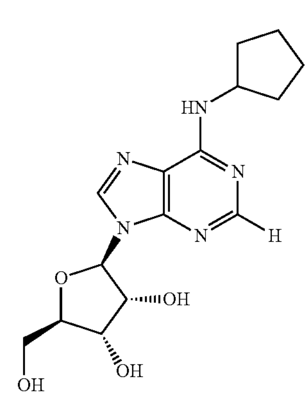

(2R,3R,4S,5R)-2-(6-(cyclopentylamino)-9H-purin-9-yl)-5-(hydroxymethyl)tetrahydrofuran-3,4-diol ($N^6$-cyclopentyl adenosine (CPA)), and Compound J

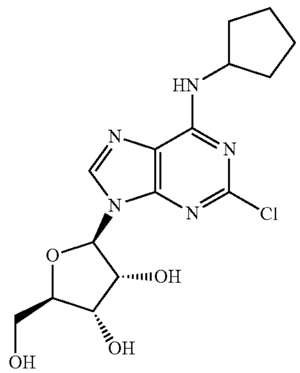

(2R,3R,4S,5R)-2-(2-chloro-6-(cyclopentylamino)-9H-purin-9-yl)-5-(hydroxymethyl)tetrahydrofuran-3,4-diol (2-chloro-$N^6$-cyclopentyl adenosine (CCPA)) or pharmaceutically acceptable salts thereof.

7. The method according to claim 1 wherein the $A_1$ receptor agonist compound is ((2R,3S,4R,5R)-5-(6-(cyclopentylamino)-9H-purin-9-yl)-3,4-dihydroxytetrahydrofuran-2-yl) methyl nitrate.

8. A method of treating elevated IOP and associated diseases and conditions caused by elevated IOP in a subject in need thereof by administering an effective amount of (i) an adenosine receptor $A_1$ agonist compound of Formula (I)

(I)

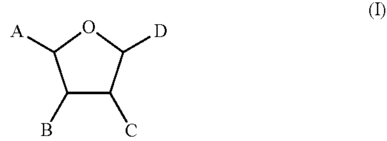

or a pharmaceutically acceptable salt thereof, wherein

A is —$CH_2OH$, —$CH_2ONO_2$ or —$CH_2OSO_3H$;

B and C are —OH;

D is

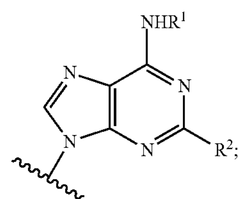

A and B are trans with respect to each other;

B and C are cis with respect to each other;

C and D are cis or trans with respect to each other;

$R^1$ is —H, —$C_1$-$C_{10}$ alkyl, -aryl, -3- to 7-membered monocyclic heterocyclyl, -8- to 12-membered bicyclic heterocyclyl, —$C_3$-$C_8$ monocyclic cycloalkyl, —$C_3$-$C_8$ monocyclic cycloalkenyl, —$C_8$-$C_{12}$ bicyclic cycloalkyl, —$C_8$-$C_{12}$ bicyclic cycloalkenyl —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), or —$(CH_2)_n$-aryl;

$R^2$ is —H, halo, —CN, —$NHR^4$, —$NHC(O)R^4$, —NHC(O)$OR^4$, —$NHC(O)NHR^4$, —$NHNHC(O)R^4$, —$NHNHC(O)OR^4$, —$NHNHC(O)NHR^4$, or —NH—N═$C(R^6)R^7$;

$R^4$ is —$C_1$-$C_{15}$ alkyl, -aryl, —$(CH_2)_n$-aryl, —$(CH_2)_n$-(3- to 7-membered monocyclic heterocyclyl), —$(CH_2)_n$-(8- to 12-membered bicyclic-heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —C≡C—($C_1$-$C_{10}$ alkyl) or —C≡C-aryl;

$R^6$ is —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic-heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), —$(CH_2)_n$—($C_8$-$C_{12}$ bicyclic cycloalkenyl), —$(CH_2)_n$—($C_3$-$C_8$ monocyclic cycloalkenyl), -phenylene-$(CH_2)_n$COOH, or -phenylene-$(CH_2)$—COO—($C_1$-$C_{10}$ alkyl);

$R^7$ is —H, —$C_1$-$C_{10}$ alkyl, -aryl, —$(CH_2)_n$-aryl, —$(CH_2)_n$-(3- to 7-membered monocyclic heterocyclyl), —$(CH_2)_n$-(8- to 12-membered bicyclic-heterocyclyl), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkenyl) or —$(CH_2)_n$—($C_8$-$C_{12}$ bicyclic cycloalkyl) and each n is independently an integer ranging from 1 to 5, and (ii) the prostaglandin analog, latanoprost.

9. The method according to claim 8 wherein the $A_1$ receptor agonist compound is applied to an eye of the subject in need thereof, simultaneously, separately or sequentially to the application of the prostaglandin analog, latanoprost, to the eye of the subject.

10. The method according to claim 8 wherein the $A_1$ receptor agonist compound is applied to an eye of the subject in need thereof, simultaneously to the application of the prostaglandin analog, latanoprost, to the eye of the subject.

11. The method according to claim 8 wherein the $A_1$ receptor agonist compound is applied to an eye of the subject in need thereof, sequentially to the application of the prostaglandin analog, latanoprost, to the eye of the subject.

12. The method according to claim 8 wherein the compound of Formula (I) is selected from the group consisting of:

Compound A

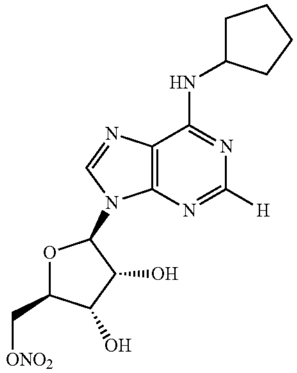

((2R,3S,4R,5R)-5-(6-(cyclopentylamino)-9H-purin-9-yl)-3,4-dihydroxytetrahydrofuran-2-yl)methyl nitrate, Compound B

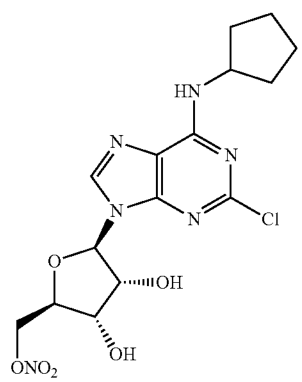

((2R,3S,4R,5R)-5-(2-chloro-6-(cyclopentylamino)-9H-purin-9-yl)-3,4-dihydroxytetrahydrofuran-2-yl)methyl nitrate, Compound C

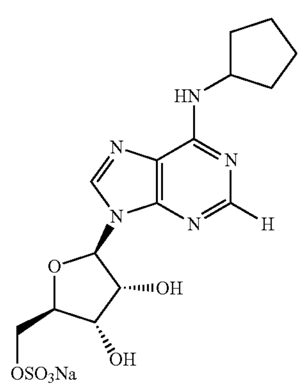

sodium ((2R,3S,4R,5R)-5-(6-(cyclopentylamino)-9H-purin-9-yl)-3,4-dihydroxytetrahydrofuran-2-yl)methyl sulfate, Compound D

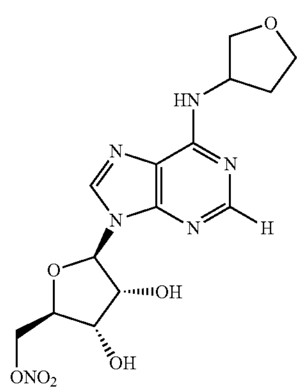

((2R,3S,4R,5R)-3,4-dihydroxy-5-(6-(tetrahydrofuran-3-ylamino)-9H-purin-9-yl)tetrahydrofuran-2-yl)methyl nitrate, Compound E

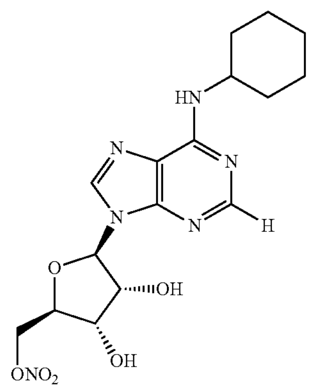

((2R,3S,4R,5R)-5-(6-(cyclohexylamino)-9H-purin-9-yl)-3,4-dihydroxytetrahydrofuran-2-yl)methyl nitrate, Compound F ((2R,3S,4R,5R)-5-(6-(bicycle-[2.2.1]-heptan-2-ylamino)-9H-purin-9-yl)-3,4-dihydroxytetrahydrofuran-2-yl) methyl nitrate, Compound G

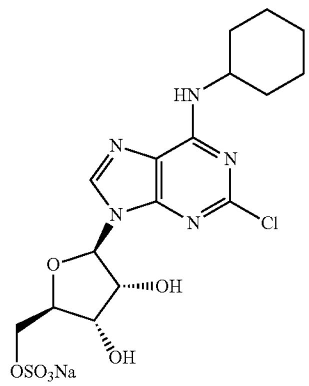

sodium ((2R,3S,4R,5R)-5-(2-chloro-6-(cyclohexylamino)-9H-purin-9-yl)-3,4-dihydroxytetrahydrofuran-2-yl)methyl sulfate, Compound H

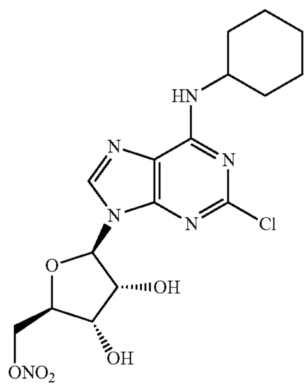

((2R,3S,4R,5R)-5-(2-chloro-6-(cyclohexylamino)-9H-purin-9-yl)-3,4-dihydroxytetrahydrofuran-2-yl)methyl nitrate Compound I

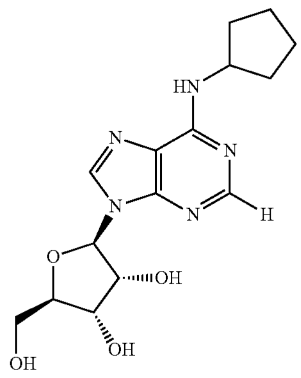

(2R,3R,4S,5R)-2-(6-(cyclopentylamino)-9H-purin-9-yl)-5-(hydroxymethyl)tetrahydrofuran-3,4-diol ($N^6$-cyclopentyl adenosine (CPA)), and Compound J

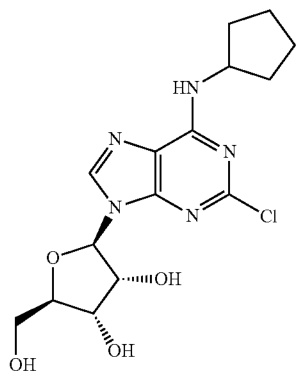

(2R,3R,4S,5R)-2-(2-chloro-6-(cyclopentylamino)-9H-purin-9-yl)-5-(hydroxymethyl)tetrahydrofuran-3,4-diol (2-chloro-$N^6$-cyclopentyl adenosine (CCPA)) or pharmaceutically acceptable salts thereof.

13. The method according to claim 8 wherein the $A_1$ receptor agonist compound is ((2R,3S,4R,5R)-5-(6-(cyclopentylamino)-9H-purin-9-yl)-3,4-dihydroxytetrahydrofuran-2-yl)methyl nitrate.

14. A method of treating elevated IOP and associated diseases and conditions caused by elevated IOP in a subject in need thereof by administering an effective amount of an adenosine receptor $A_1$ agonist Compound A, ((2R,3S,4R,5R)-5-(6-(cyclopentylamino)-9H-purin-9-yl)-3,4-dihydroxytetrahydrofuran-2-yl)methyl nitrate, and the prostaglandin analog is latanoprost.

* * * * *

UNITED STATES PATENT AND TRADEMARK OFFICE

CERTIFICATE OF CORRECTION

PATENT NO. : 8,877,732 B2
APPLICATION NO. : 13/004380
DATED : November 4, 2014
INVENTOR(S) : Kim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this
Ninth Day of February, 2016

Michelle K. Lee

Michelle K. Lee
*Director of the United States Patent and Trademark Office*